United States Patent
Nakamura et al.

(10) Patent No.: US 11,436,859 B2
(45) Date of Patent: Sep. 6, 2022

(54) FINGERPRINT DETECTION DEVICE AND DISPLAY DEVICE WITH FINGERPRINT DETECTION DEVICE

(71) Applicant: Japan Display Inc., Tokyo (JP)

(72) Inventors: Takashi Nakamura, Minato-ku (JP); Makoto Uchida, Minato-ku (JP); Takanori Tsunashima, Minato-ku (JP); Hirofumi Kato, Minato-ku (JP); Akio Takimoto, Minato-ku (JP)

(73) Assignee: Japan Display Inc., Tokyo (JP)

( * ) Notice: Subject to any disclaimer, the term of this patent is extended or adjusted under 35 U.S.C. 154(b) by 0 days.

(21) Appl. No.: 17/233,650

(22) Filed: Apr. 19, 2021

(65) Prior Publication Data

US 2021/0240963 A1 Aug. 5, 2021

Related U.S. Application Data

(63) Continuation of application No. PCT/JP2019/034594, filed on Sep. 3, 2019.

(30) Foreign Application Priority Data

Oct. 24, 2018 (JP) .............................. JP2018-200355

(51) Int. Cl.
*G06V 40/13* (2022.01)
(52) U.S. Cl.
CPC ................................ *G06V 40/1318* (2022.01)
(58) Field of Classification Search
CPC ............ G06K 9/0004; G06F 3/041661; G06V 40/1318
See application file for complete search history.

(56) References Cited

U.S. PATENT DOCUMENTS

| | | | |
|---|---|---|---|
| 2003/0090650 A1* | 5/2003 | Fujieda | G06K 9/0004 356/71 |
| 2003/0155483 A1 | 8/2003 | Yokomichi et al. | |
| 2005/0179795 A1 | 8/2005 | Funatsu et al. | |
| 2012/0099304 A1* | 4/2012 | Kim | G06F 3/042 362/231 |
| 2016/0266695 A1* | 9/2016 | Bae | G06F 3/04166 |
| 2017/0200037 A1* | 7/2017 | Hong | G06F 3/041661 |
| 2018/0012069 A1 | 1/2018 | Chung et al. | |
| 2018/0150671 A1 | 5/2018 | Choo et al. | |

FOREIGN PATENT DOCUMENTS

| | | |
|---|---|---|
| JP | 2003-244397 A | 8/2003 |
| JP | 2005-229373 A | 8/2005 |
| JP | 2009-009403 A | 1/2009 |
| JP | 2018-087973 A | 6/2018 |

OTHER PUBLICATIONS

International Search Report dated Dec. 3, 2019 in PCT/JP2019/034594 filed on Sep. 3, 2019, 2 pages.

* cited by examiner

*Primary Examiner* — Stephen G Sherman
(74) *Attorney, Agent, or Firm* — Maier & Maier, PLLC

(57) ABSTRACT

A fingerprint detection device includes a substrate, a plurality of photoelectric conversion elements that are provided to the substrate and each output a signal corresponding to light emitted thereto, a plurality of signal lines coupled to the photoelectric conversion elements, a detection circuit that is electrically coupled to the photoelectric conversion elements through the signal lines, and a signal line selection circuit that switches the number of the signal lines to be coupled to the one detection circuit.

5 Claims, 21 Drawing Sheets

FINGERPRINT DETECTION DEVICE AND DISPLAY DEVICE WITH FINGERPRINT DETECTION DEVICE

CROSS-REFERENCE TO RELATED APPLICATION

This application claims the benefit of priority from Japanese Patent Application No. 2018-200355 filed on Oct. 24, 2018 and International Patent Application No. PCT/JP2019/034594 filed on Sep. 3, 2019, the entire contents of which are incorporated herein by reference.

BACKGROUND

1. Technical Field

The present disclosure relates to a fingerprint detection device and a display device with a fingerprint detection device.

2. Description of the Related Art

In recent years, optical fingerprint sensors (refer, for example, to United States Patent Application Publication No. 2018/0012069) are known as fingerprint sensors used, for example, for personal authentication. Such an optical fingerprint sensor includes a photoelectric conversion element that outputs a signal that changes with an amount of light irradiated thereto. In the fingerprint sensor described in United States Patent Application Publication No. 2018/0012069, a plurality of photoelectric conversion elements, such as photodiodes, are arranged on a semiconductor substrate.

The fingerprint sensor is required to detect various types of information on a detection target object in addition to a shape of a fingerprint of the detection target object, such as a finger or a palm. If the fingerprint is detected at a high-definition resolution, the detection may be difficult to be properly performed in a plurality of detection operations.

SUMMARY

A fingerprint detection device according to an aspect includes: a substrate; a plurality of photoelectric conversion elements provided to the substrate, each being configured to output a signal corresponding to light emitted thereto; a plurality of signal lines coupled to the photoelectric conversion elements; a detection circuit electrically coupled to the photoelectric conversion elements through the signal lines; and a signal line selection circuit configured to switch a number of the signal lines to be coupled to the one detection circuit.

A display device with a fingerprint detection device according to an aspect, includes: the fingerprint detection device; and a display panel including a display element for displaying an image and disposed so as to face the substrate.

DETAILED DESCRIPTION

Figure 1:
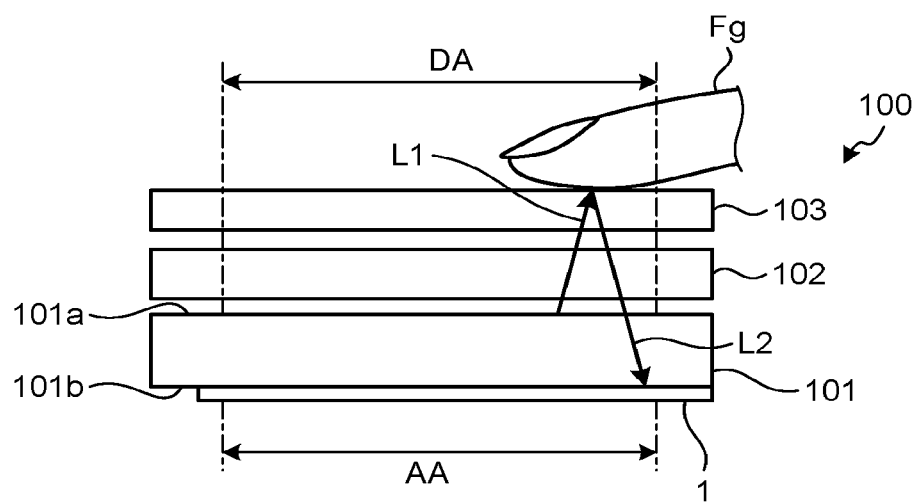
FIG. 1 is a sectional view illustrating a schematic sectional configuration of a display device with a fingerprint detection device according to a first embodiment.

The following describes embodiments for carrying out the present disclosure in detail with reference to the drawings.

The present disclosure is not limited to the description of the embodiments given below. Components described below include those easily conceivable by those skilled in the art or those substantially identical thereto. Moreover, the components described below can be appropriately combined. The disclosure is merely an example, and the present disclosure naturally encompasses appropriate modifications easily conceivable by those skilled in the art while maintaining the gist of the disclosure. To further clarify the description, widths, thicknesses, shapes, and other properties of various parts are schematically illustrated as compared with actual aspects thereof, in some cases. However, they are merely examples, and interpretation of the present disclosure is not limited thereto. The same element as that illustrated in a drawing that has already been discussed is denoted by the same reference numeral through the description and the drawings, and detailed description thereof will not be repeated in some cases where appropriate.

In this disclosure, when an element is described as being "on" another element, the element can be directly on the other element, or there can be one or more elements between the element and the other element.

First Embodiment

FIG. 1 is a sectional view illustrating a schematic sectional configuration of a display device with a fingerprint detection device according to a first embodiment. As illustrated in FIG. 1, a display device 100 with a fingerprint detection device includes a fingerprint detection device 1, a display panel 101, a touchscreen panel 102, and a cover glass 103. The display panel 101 includes a plurality of display elements for displaying an image, and may be, for example, an organic electroluminescent (EL) (organic light-emitting diode (OLED)) display panel or an inorganic EL (micro-LED or mini-LED) display using light-emitting elements as the display elements. Alternatively, the display panel 101 may be a liquid crystal display (LCD) panel using liquid crystal elements as the display elements, or an electrophoretic display (EPD) panel using electrophoretic elements as the display elements.

The display panel 101 has a first principal surface 101a and a second principal surface 101b on a side opposite to the first principal surface 101a. The first principal surface 101a is a display surface on which the image is displayed, and emits light L1 from the display elements toward the cover glass 103. The first principal surface 101a has a display area DA in which the image is displayed.

The touchscreen panel 102 is provided on the first principal surface 101a of the display panel 101. The touchscreen panel 102 uses, for example, a self-capacitance method to detect a finger Fg in contact with or in proximity to a surface of the cover glass 103. The touchscreen panel 102 has light transmittance and can transmit the light L1 and reflected light L2. The light L2 includes light reflected on an interface between the cover glass 103 and air, and light reflected on a surface of the finger Fg. The display device 100 with a fingerprint detection device may have a configuration not including the touchscreen panel 102. The display panel 101 may be integrated with the touchscreen panel 102 or may incorporate a function or functions of the touchscreen panel 102.

The cover glass 103 is a member for protecting the display panel 101 and the touchscreen panel 102 and covers the display panel 101 and the touchscreen panel 102. The cover glass 103 is, for example, a glass substrate. The member is not limited to the cover glass 103. For example, a resin substrate may be provided on the touchscreen panel 102. The surface of the cover glass 103 serves as a detection surface on which the finger Fg is detected.

The fingerprint detection device 1 is provided so as to face the second principal surface 101b of the display panel 101. In other words, the display panel 101 is provided between the fingerprint detection device 1 and the touchscreen panel 102. The fingerprint detection device 1 performs a first detection mode M1, and a second detection mode M2 of detecting the light L2 at a detection pitch different from that in the first detection mode M1. In the first detection mode M1, the fingerprint detection device 1 can detect asperities on the surface of the finger Fg by detecting the light L2 reflected on the interface between the cover glass 103 and air. In the second detection mode M2, the fingerprint detection device 1 can detect biological information by detecting light L12 reflected in the finger Fg (refer to FIG. 15). Since the fingerprint detection device 1 can be easily increased in area, a detection area AA of the fingerprint detection device 1 is provided so as to face the entire display area DA of the display panel 101. The detection area AA is not limited to this configuration and may partially face the display area DA of the display panel 101.

Figure 2:
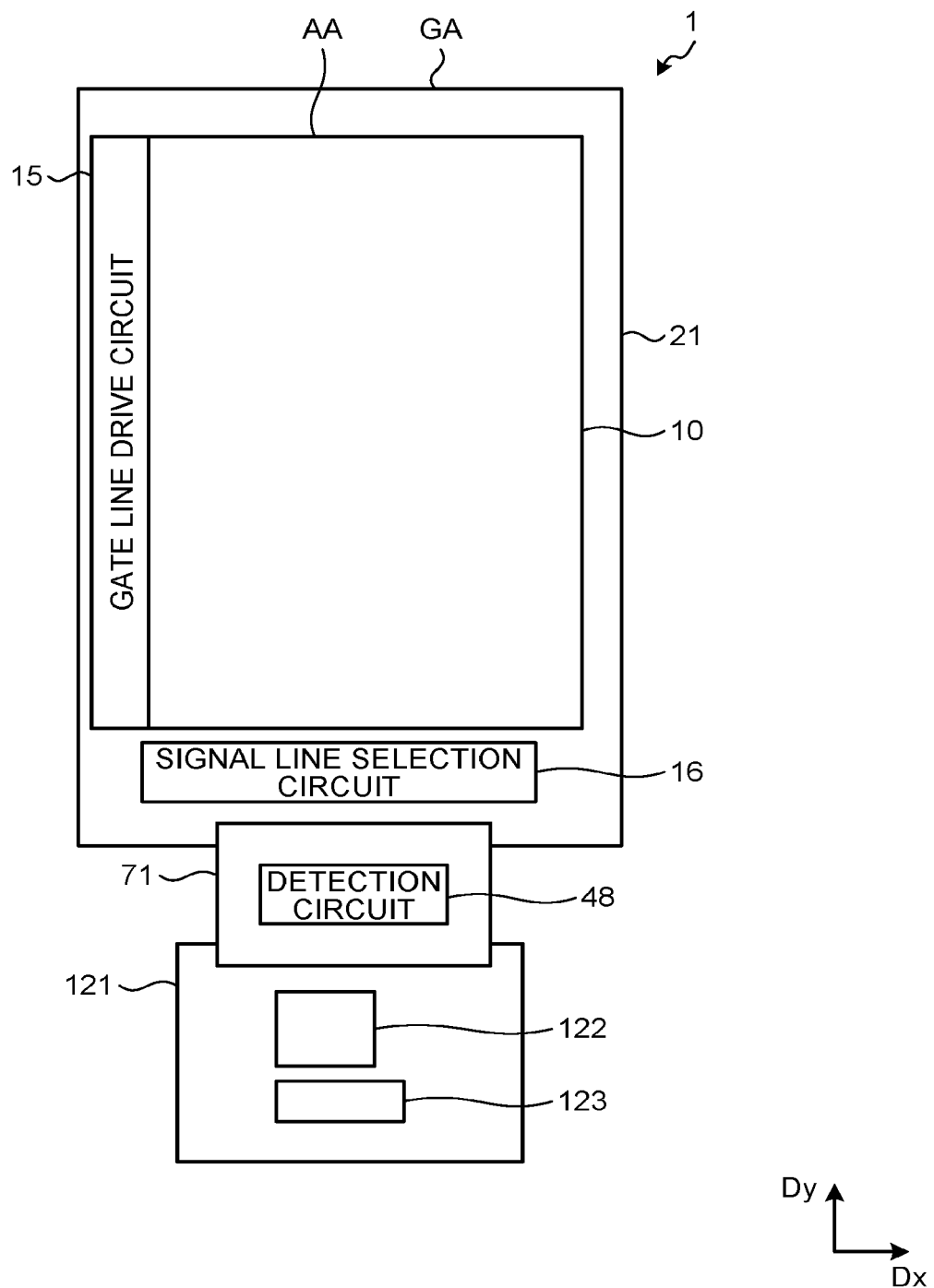
FIG. 2 is a plan view illustrating the fingerprint detection device according to the first embodiment.

FIG. 2 is a plan view illustrating the fingerprint detection device according to the first embodiment. As illustrated in FIG. 2, the fingerprint detection device 1 includes a first substrate 21, a sensor 10, a gate line drive circuit 15, a signal line selection circuit 16, a detection circuit 48, a control circuit 122, and a power supply circuit 123.

A control board 121 is electrically coupled to the first substrate 21 through a flexible printed circuit board 71. The flexible printed circuit board 71 is provided with the detection circuit 48. The control board 121 is provided with the control circuit 122 and the power supply circuit 123. The control circuit 122 is, for example, a field programmable gate array (FPGA). The control circuit 122 supplies control signals to the sensor 10, the gate line drive circuit 15, and the signal line selection circuit 16 to control a detection operation of the sensor 10. The power supply circuit 123 supplies voltage signals including, for example, a sensor power supply signal VDDSNS (refer to FIG. 5) to the sensor 10, the gate line drive circuit 15, and the signal line selection circuit 16.

The first substrate 21 has the detection area AA and a peripheral area GA. The detection area AA is an area provided with a plurality of photodiodes PD (refer to FIG. 5) included in the sensor 10. The peripheral area GA is an area between the outer circumference of the detection area AA and edges of the first substrate 21 and is an area not overlapping the photodiodes PD.

The gate line drive circuit 15 and the signal line selection circuit 16 are provided in the peripheral area GA. Specifically, the gate line drive circuit 15 is provided in an area of the peripheral area GA extending in a second direction Dy, and the signal line selection circuit 16 is provided in an area of the peripheral area GA extending in a first direction Dx and is provided between the sensor 10 and the detection circuit 48.

The first direction Dx is a direction in a plane parallel to the first substrate 21. The second direction Dy is a direction in a plane parallel to the first substrate 21 and is a direction orthogonal to the first direction Dx. The second direction Dy may intersect the first direction Dx without being orthogonal thereto.

Figure 3:
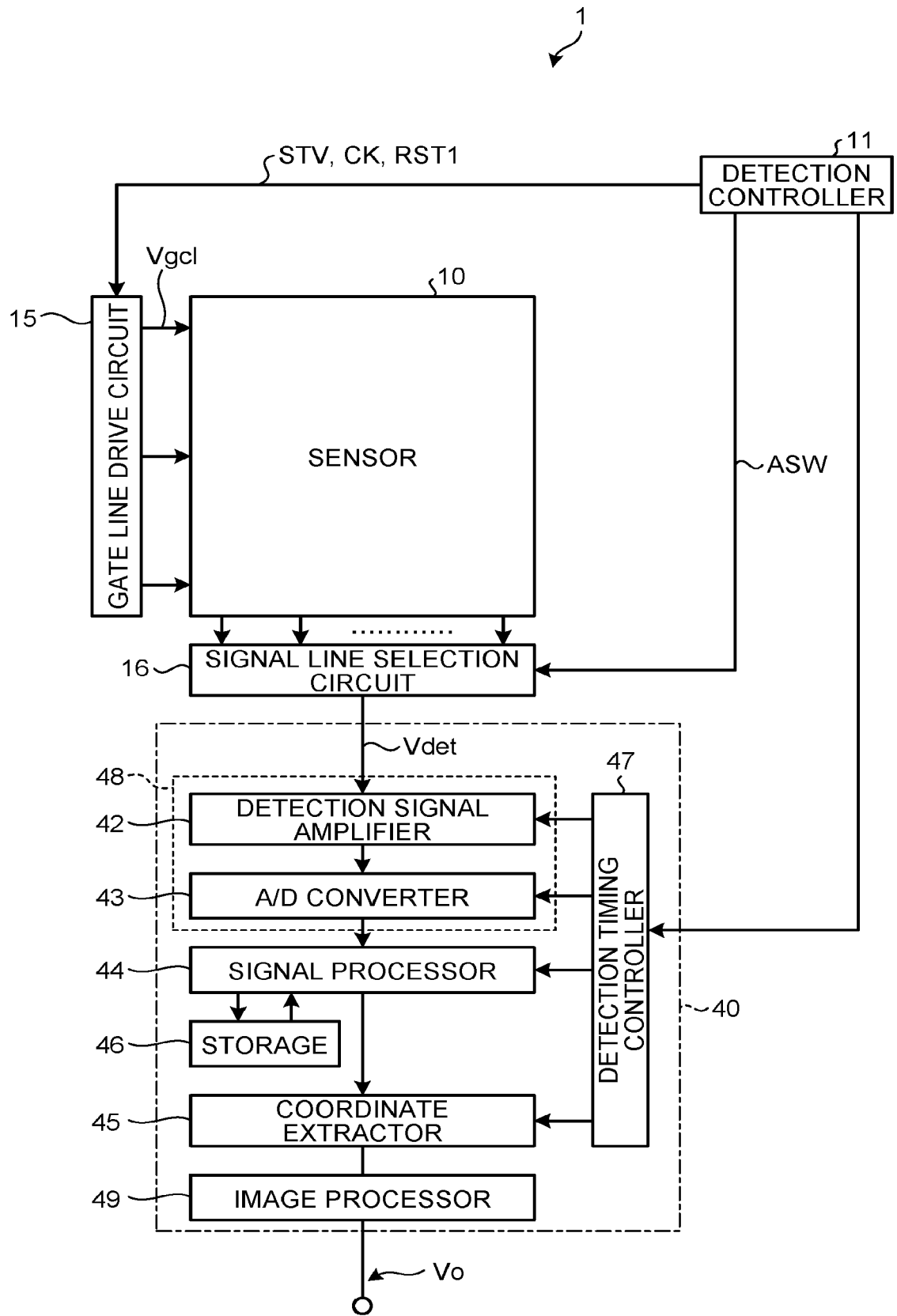
FIG. 3 is a block diagram illustrating a configuration example of the fingerprint detection device according to the first embodiment.

FIG. 3 is a block diagram illustrating a configuration example of the fingerprint detection device according to the first embodiment. As illustrated in FIG. 3, the fingerprint detection device 1 further includes a detection controller 11 and a detector 40. Some or all functions of the detection controller 11 are included in the control circuit 122. Some or all functions of the detector 40 except those of the detection circuit 48 are included in the control circuit 122.

The sensor 10 is an optical sensor including the photodiodes PD serving as photoelectric conversion elements. Each of the photodiodes PD included in the sensor 10 outputs an electrical signal corresponding to light emitted thereto as a detection signal Vdet to the signal line selection circuit 16. The sensor 10 performs the detection in response to a gate drive signal Vgcl supplied from the gate line drive circuit 15.

The detection controller 11 is a circuit that supplies respective control signals to the gate line drive circuit 15, the signal line selection circuit 16, and the detector 40 to control operations thereof. The detection controller 11 supplies various control signals including, for example, a start signal STV, a clock signal CK, and a reset signal RST1 to the gate line drive circuit 15. The detection controller 11 also supplies various control signals including, for example, a selection signal ASW to the signal line selection circuit 16.

The gate line drive circuit 15 is a circuit that drives a plurality of first gate lines GCL (refer to FIG. 4) based on the various control signals. The gate line drive circuit 15 sequentially or simultaneously selects the first gate lines GCL and supplies the gate drive signal Vgcl to the selected first gate lines GCL. Through this operation, the gate line drive circuit 15 selects the photodiodes PD coupled to the first gate lines GCL.

Figure 4:
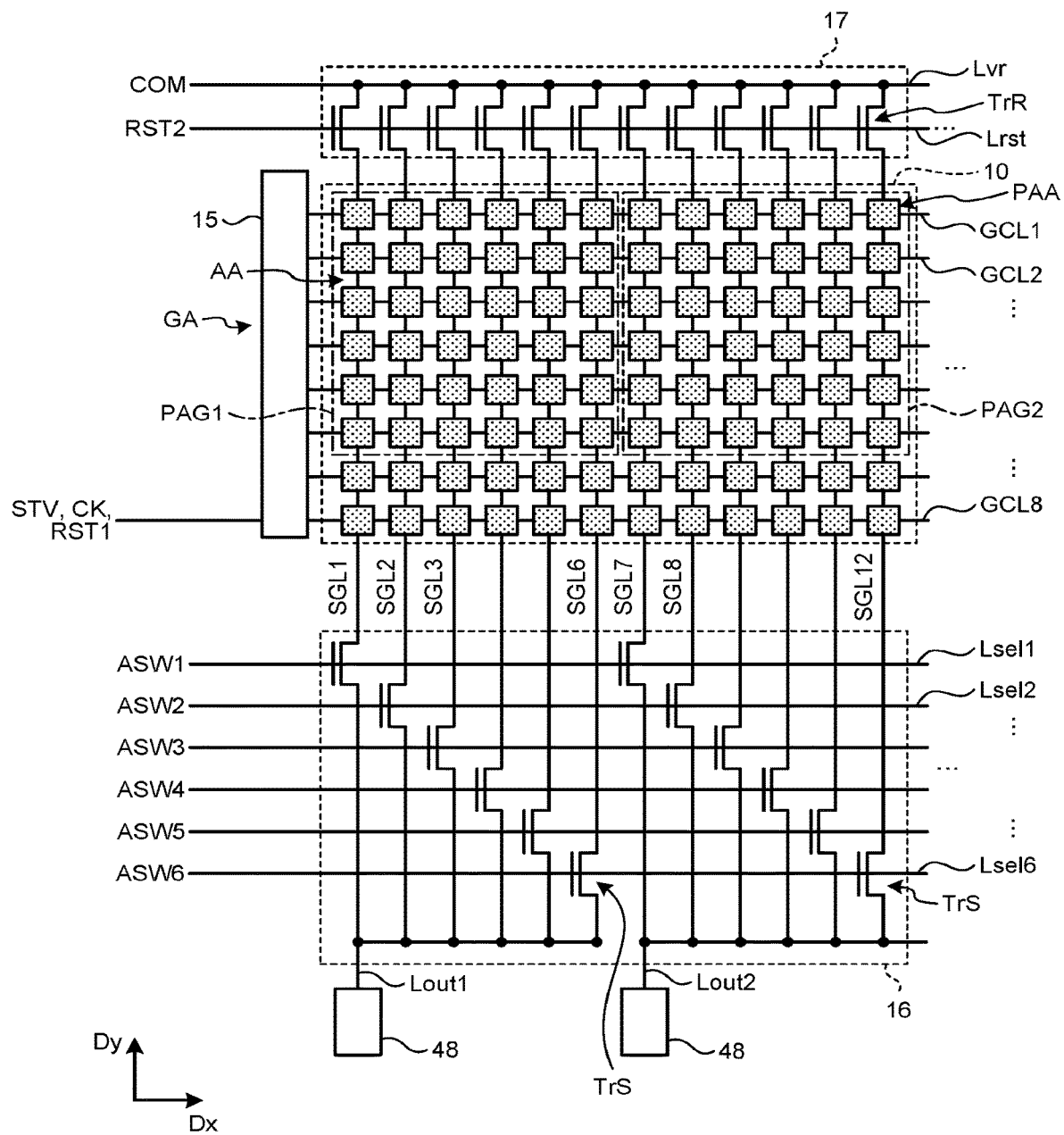
FIG. 4 is a circuit diagram illustrating the fingerprint detection device.

The signal line selection circuit 16 is a switch circuit that sequentially or simultaneously selects a plurality of signal lines SGL (refer to FIG. 4). The signal line selection circuit 16 is, for example, a multiplexer. The signal line selection circuit 16 couples the selected signal lines SGL to the detection circuit 48 based on the selection signal ASW supplied from the detection controller 11. Through this operation, the signal line selection circuit 16 outputs the detection signal Vdet of each of the photodiodes PD to the detector 40.

The detector 40 includes the detection circuit 48, a signal processor 44, a coordinate extractor 45, a storage 46, a detection timing controller 47, and an image processor 49. The detection timing controller 47 controls, based on a control signal supplied from the detection controller 11, the detection circuit 48, the signal processor 44, the coordinate extractor 45, and the image processor 49 so as to operate in synchronization with one another.

The detection circuit 48 is, for example, an analog front end (AFE) circuit. The detection circuit 48 is a signal processing circuit having functions of at least a detection signal amplifier 42 and an analog-to-digital (A/D) converter 43. The detection signal amplifier 42 amplifies the detection signal Vdet. The A/D converter 43 converts an analog signal output from the detection signal amplifier 42 into a digital signal.

The signal processor 44 is a logic circuit that detects a predetermined physical quantity received by the sensor 10 based on an output signal of the detection circuit 48. When the finger is in contact with or in proximity to the detection surface, the signal processor 44 can detect the asperities on the surface of the finger Fg or the palm based on the signal from the detection circuit 48. The signal processor 44 can also detect the biological information based on the signal from the detection circuit 48. The biological information is, for example, a blood vessel image and/or pulsation of the finger Fg or the palm.

The storage 46 temporarily stores a signal calculated by the signal processor 44. The storage 46 may be, for example, a random access memory (RAN) or a register circuit.

The coordinate extractor 45 is a logic circuit that obtains, when the contact or the proximity of a finger or the like is detected by the signal processor 44, detection coordinates of the asperities on the surface of, for example, the finger. The coordinate extractor 45 is also a logic circuit that obtains detection coordinates of blood vessels of the finger Fg or the palm. The image processor 49 combines the detection signals Vdet output from the respective photodiodes PD of the sensor 10 to generate two-dimensional information representing a shape of the asperities on the surface of, for example, the finger Fg and two-dimensional information representing a shape of the blood vessels of the finger Fg or the palm. The coordinate extractor 45 may output the detection signals Vdet as sensor outputs Vo, without calculating the detection coordinates. There may be a case where the coordinate extractor 45 and the image processor 49 are not included in the detector 40.

Figure 5:
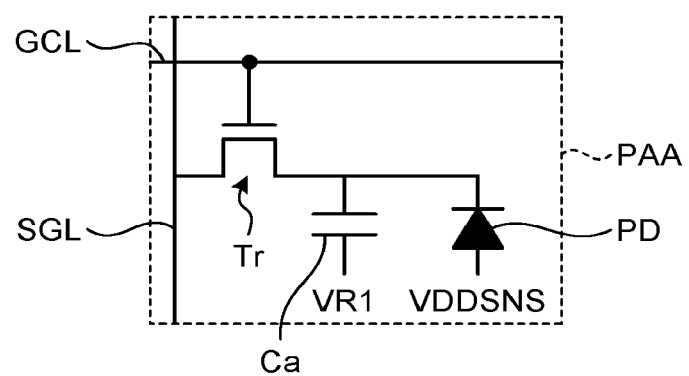
FIG. 5 is a circuit diagram illustrating a partial detection area.

The following describes a circuit configuration example of the fingerprint detection device 1. FIG. 4 is a circuit diagram illustrating the fingerprint detection device. FIG. 5 is a circuit diagram illustrating a partial detection area.

As illustrated in FIG. 4, the sensor 10 has a plurality of partial detection areas PAA arranged in a matrix having a row-column configuration. Each of the partial detection areas PAA is provided with the photodiode PD.

The first gate lines GCL extend in the first direction Dx and are coupled to the partial detection areas PAA arranged in the first direction Dx. A plurality of first gate lines GCL1, GCL2, . . . , GCL8 are arranged in the second direction Dy and are each coupled to the gate line drive circuit 15. In the following description, the first gate lines GCL1, GCL2, . . . , GCL8 will each be simply referred to as the first gate line GCL when they need not be distinguished from one another. For ease of understanding of the description, FIG. 4 illustrates eight first gate lines GCL. However, this is merely an example, and m first gate lines GCL (where m is eight or larger and is, for example, 256) may be arranged.

The signal lines SGL extend in the second direction Dy and are coupled to the photodiodes PD of the partial detection areas PAA arranged in the second direction Dy. A plurality of signal lines SGL1, SGL2, . . . , SGL12 are arranged in the first direction Dx and are each coupled to the signal line selection circuit 16 and a reset circuit 17. For ease of understanding of the description, 12 signal lines SGL are illustrated. However, this is merely an example, and n signal lines SGL (where n is 12 or larger, and is, for example, 252) may be arranged. In FIG. 4, the sensor 10 is provided between the signal line selection circuit 16 and the reset circuit 17. The configuration is not limited thereto. The signal line selection circuit 16 and the reset circuit 17 may be coupled to ends in the same direction of the signal lines SGL.

The gate line drive circuit 15 receives the various control signals such as the start signal STV, the clock signal CK, and the reset signal RST1 from the control circuit 122 (refer to FIG. 2). In the first detection mode M1 of detecting the asperities on the surface of, for example, the finger Fg, the gate line drive circuit 15 sequentially selects the first gate lines GCL1, GCL2, . . . , GCL8 in a time-division manner based on the control signals. The gate line drive circuit 15 supplies the gate drive signal Vgcl to the selected one of the first gate lines GCL. This operation supplies the gate drive signal Vgcl to a plurality of first switching elements Tr coupled to the first gate line GCL, and more than one of the partial detection areas PAA arranged in the first direction Dx are selected as detection targets.

In the second detection mode M2, the gate line drive circuit 15 simultaneously selects a predetermined number of the first gate lines GCL from among the first gate lines GCL1, GCL2, ..., GCL8 based on the control signals. For example, the gate line drive circuit 15 simultaneously selects six first gate lines: the first gate lines GCL1 to GCL6, and supplies thereto the gate drive signals Vgcl. The gate line drive circuit 15 supplies the gate drive signals Vgcl through the selected six first gate lines GCL to the first switching elements Tr. Through this operation, detection area groups PAG1 and PAG2 each including more than one of the partial detection areas PAA arranged in the first direction Dx and the second direction Dy are selected as the respective detection targets. The gate line drive circuit 15 drives the predetermined number of the first gate lines GCL in a bundle, and sequentially supplies the gate drive signal Vgcl to each predetermined number of the first gate lines GCL.

The signal line selection circuit 16 includes a plurality of selection signal lines Lsel, a plurality of output signal lines Lout, and third switching elements TrS. The third switching elements TrS are provided corresponding to the signal lines SGL. Six signal lines SGL1, SGL2, ..., SGL6 are coupled to a common output signal line Lout1. Six signal lines SGL7, SGL8, ..., SGL12 are coupled to a common output signal line Lout2. The output signal lines Lout1 and Lout2 are each coupled to the detection circuit 48.

The signal lines SGL1, SGL2, ..., SGL6 are grouped into a first signal line block, and the signal lines SGL7, SGL8, ..., SGL12 are grouped into a second signal line block. The selection signal lines Lsel are coupled to the gates of the respective third switching elements TrS included in one of the signal line blocks. One of the selection signal lines Lsel is coupled to the gates of the third switching elements TrS in the signal line blocks. Specifically, selection signal lines Lsel1, Lsel2, ..., Lsel6 are coupled to the third switching elements TrS corresponding to the signal lines SGL1, SGL2, ..., SGL6. The selection signal line Lsel1 is coupled to the third switching element TrS corresponding to the signal line SGL1 and the third switching element TrS corresponding to the signal line SGL7. The selection signal line Lsel2 is coupled to the third switching element TrS corresponding to the signal line SGL2 and the third switching element TrS corresponding to the signal line SGL8.

In the first detection mode M1, the control circuit 122 (refer to FIG. 2) sequentially supplies the selection signal ASW to the selection signal lines Lsel. This operation causes the signal line selection circuit 16 to operate the third switching elements TrS to sequentially select the signal lines SGL in one of the signal line blocks in a time-division manner. The signal line selection circuit 16 selects one of the signal lines SGL in each of the signal line blocks. The above-described configuration can reduce the number of integrated circuits (ICs) including the detection circuit 48 or the number of terminals of the ICs in the fingerprint detection device 1.

In the second detection mode M2, the control circuit 122 (refer to FIG. 2) simultaneously supplies the selection signal ASW to the selection signal lines Lsel. This operation causes the signal line selection circuit 16 to operate the third switching elements TrS to select the signal lines SGL (for example, six of the signal lines SGL) in one of the signal line blocks, and couple the signal lines SGL to the detection circuit 48. As a result, signals detected in the detection area groups PAG1 and PAG2 are output to the detection circuit 48. In this case, signals from the partial detection areas PAA (photodiodes PD) included in the detection area groups PAG1 and PAG2 are put together and output to the detection circuit 48.

In this manner, the signal line selection circuit 16 can switch the number of the signal lines SGL to be coupled to the one detection circuit 48 between the first detection mode M1 and the second detection mode M2. The fingerprint detection device 1 can perform the detection in the second detection mode M2 at a larger detection pitch than that in the first detection mode M1.

Each of the detection area groups PAG1 and PAG2 includes a total of 36 (6×6) partial detection areas PAA (photodiodes PD). However, the number of the partial detection areas PAA (photodiodes PD) included in each of the detection area groups PAG1 and PAG2 may be equal to or smaller than 35, or may be equal to or larger than 37. In the second detection mode M2, the number of the first gate lines GCL selected by the gate line drive circuit 15 may differ from the number of the signal lines SGL selected by the signal line selection circuit 16. That is, in each of the detection area groups PAG1 and PAG2, the number of the partial detection areas PAA (photodiodes PD) arranged in the first direction Dx may differ from the number of the partial detection areas PAA (photodiodes PD) arranged in the second direction Dy. Although FIG. 4 illustrates the two detection area groups PAG1 and PAG2 adjacent in the first direction Dx, three or more detection area groups PAG are arranged in the first direction Dx, and a plurality thereof are arranged in the second direction Dy. That is, the detection area groups PAG are arranged in a matrix having a row-column configuration in the first direction Dx and the second direction Dy.

As illustrated in FIG. 4, the reset circuit 17 includes a reference signal line Lvr, a reset signal line Lrst, and fourth switching elements TrR. The fourth switching elements TrR are provided corresponding to the signal lines SGL. The reference signal line Lvr is coupled to either the sources or the drains of the fourth switching elements TrR. The reset signal line Lrst is coupled to the gates of the fourth switching elements TrR.

The control circuit 122 supplies a reset signal RST2 to the reset signal line Lrst. This operation turns on the fourth switching elements TrR to electrically couple the signal lines SGL to the reference signal line Lvr. The power supply circuit 123 supplies a reference signal COM to the reference signal line Lvr. This operation supplies the reference signal COM to a capacitive element Ca (refer to FIG. 5) included in each of the partial detection areas PAA.

As illustrated in FIG. 5, the partial detection area PAA includes the photodiode PD, the capacitive element Ca, and the first switching element Tr. The first switching element Tr is provided corresponding to the photodiode PD. The first switching element Tr is fabricated from a thin-film transistor (TFT), and in this example, fabricated from an n-channel metal oxide semiconductor (MOS) thin-film transistor (TFT). The gate of the first switching element Tr is coupled to the first gate line GCL. The source of the first switching element Tr is coupled to the signal line SGL. The drain of the first switching element Tr is coupled to a cathode of the photodiode PD and the capacitive element Ca.

An anode of the photodiode PD is supplied with the sensor power supply signal VDDSNS from the power supply circuit 123. The capacitive element Ca is supplied with a reference signal VR1 that serves as an initial potential of the capacitive element Ca from the power supply circuit 123.

When the partial detection area PAA is irradiated with light, a current corresponding to an amount of the light flows through the photodiode PD. As a result, an electrical charge is stored in the capacitive element Ca. After the first switching element Tr is turned on, a current corresponding to the electrical charge stored in the capacitive element Ca flows through the signal line SGL. The signal line SGL is coupled to the detection circuit 48 through the signal line selection circuit 16. Thus, the fingerprint detection device 1 can detect a signal corresponding to the amount of the light irradiating the photodiode PD for each of the partial detection areas PAA or signals corresponding to the amounts of the light irradiating the photodiodes PD for each of the detection area groups PAG1 and PAG2.

Figure 6:
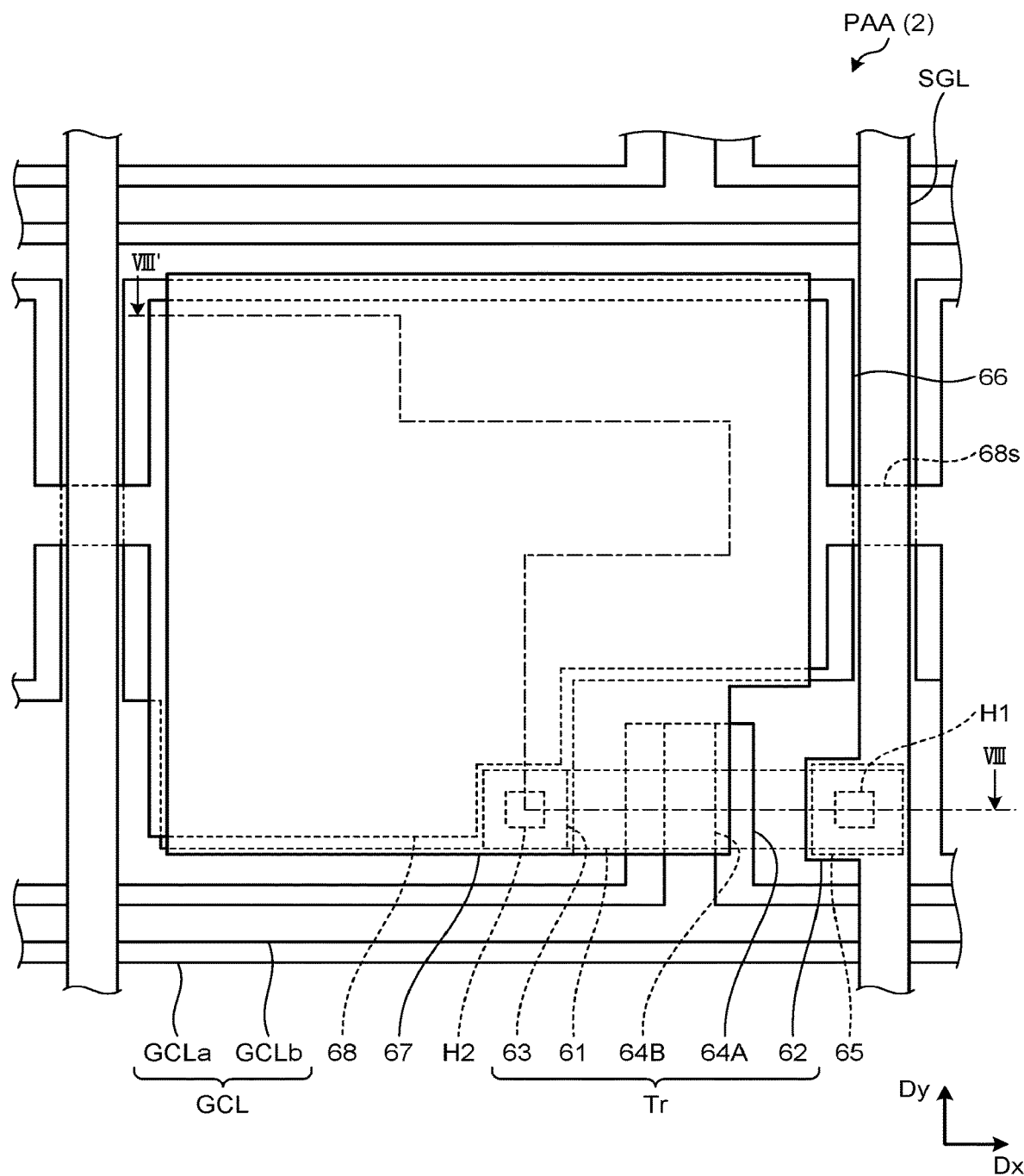
FIG. 6 is a plan view schematically illustrating a portion of the partial detection area of the fingerprint detection device according to the first embodiment.
Figure 7:
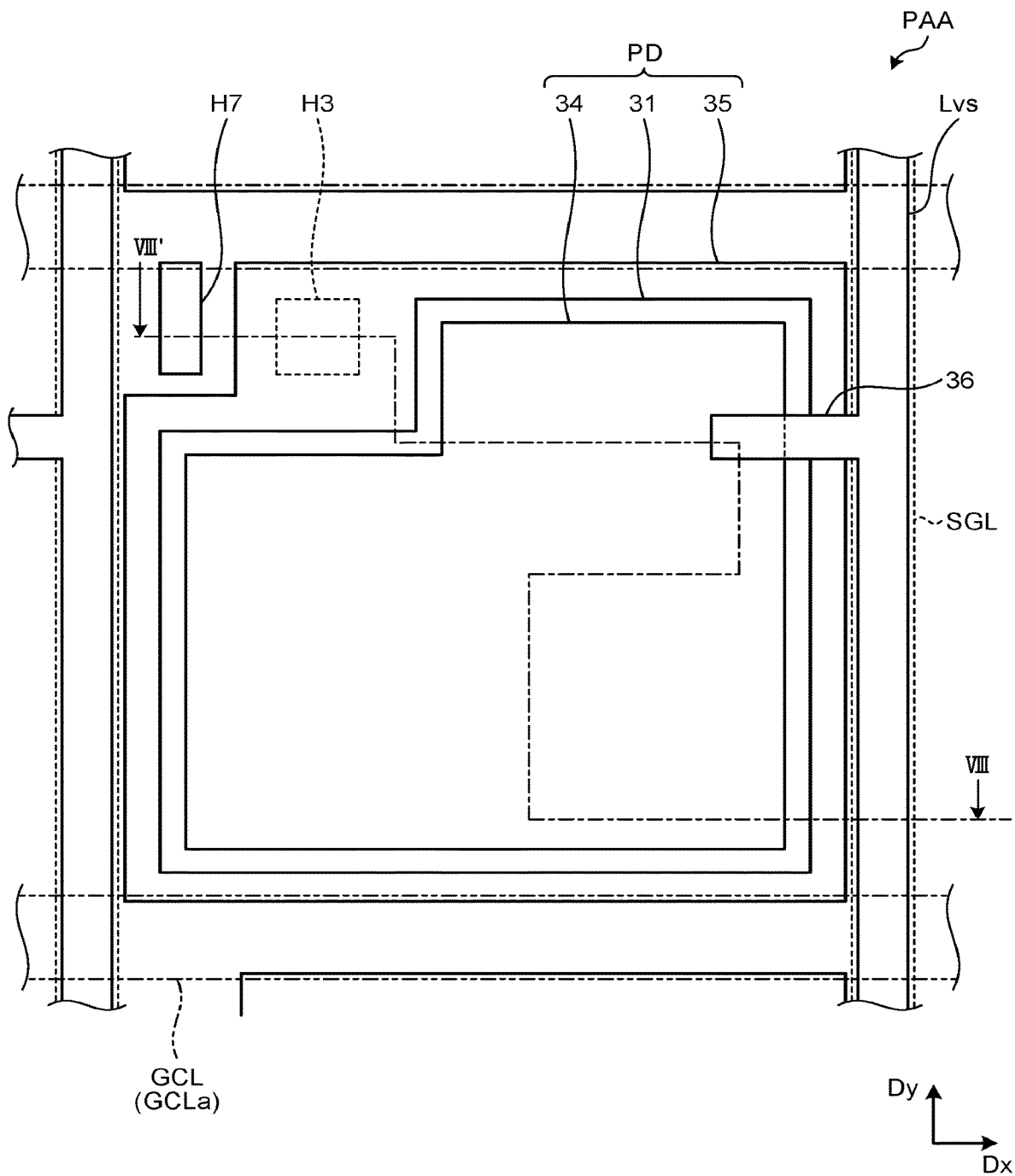
FIG. 7 is a plan view schematically illustrating a photodiode in the partial detection area of the fingerprint detection device according to the first embodiment.
Figure 8:
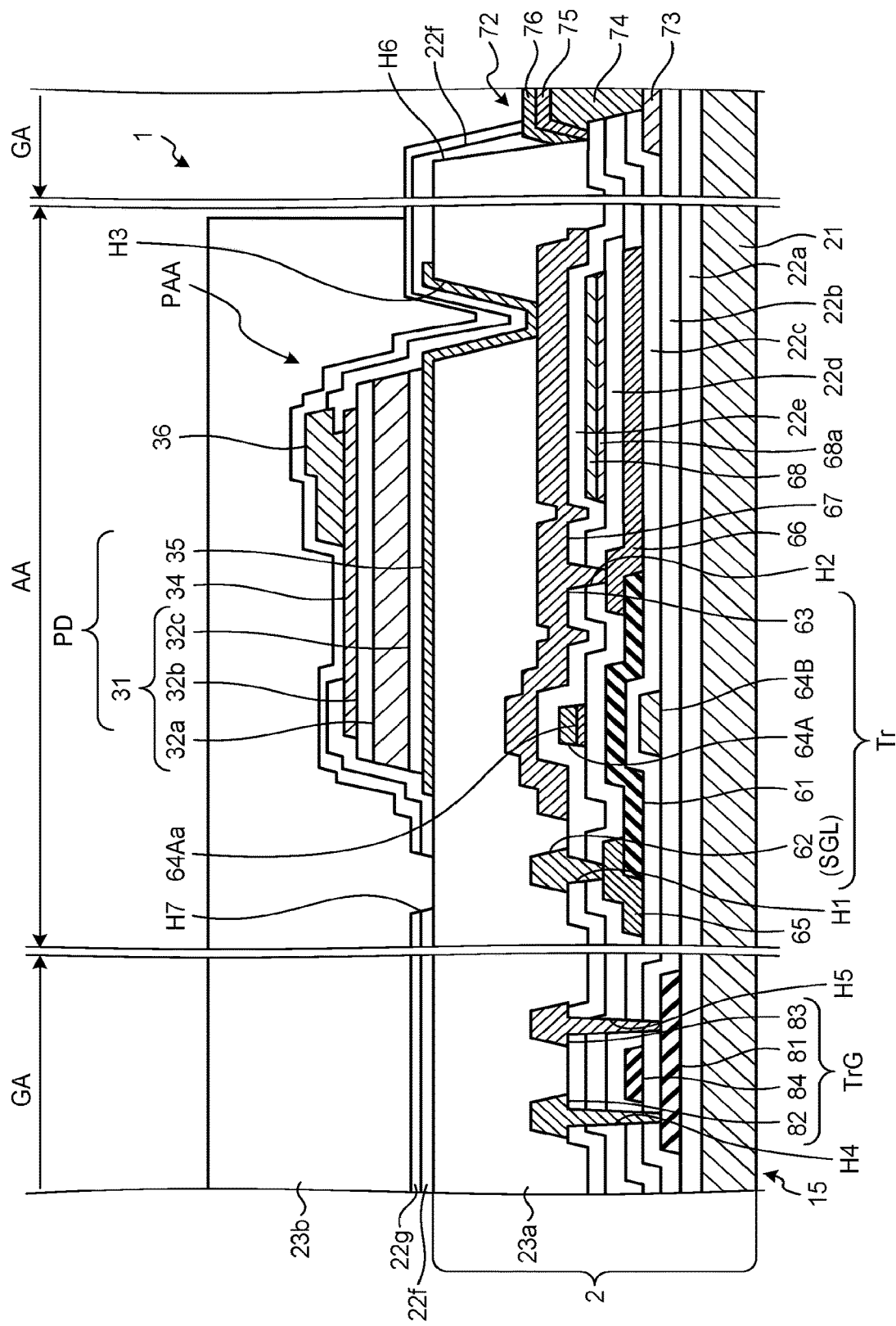
FIG. 8 is a sectional view taken along line VIII-VIII' of FIGS. 6 and 7.

The following describes a detailed configuration of the fingerprint detection device 1. FIG. 6 is a plan view schematically illustrating a portion of the partial detection area of the fingerprint detection device according to the first embodiment. FIG. 7 is a plan view schematically illustrating the photodiode in the partial detection area of the fingerprint detection device according to the first embodiment. FIG. 8 is a sectional view taken along line VIII-VIII' of FIGS. 6 and 7. FIG. 6 illustrates a configuration on a backplane 2 side of the partial detection area PAA except the photodiode PD. To illustrate a relation between a layered structure of the detection area AA and a layered structure of the peripheral area GA, FIG. 8 illustrates the section taken along line VIII-VIII' and a section of a portion of the peripheral area GA including a fifth switching element TrG in such a manner that the sections are schematically connected to each other. FIG. 8 also illustrates a section of a portion of the peripheral area GA including a terminal portion 72 in such a way it is schematically connected thereto.

In the description of the fingerprint detection device 1, in a direction orthogonal to a surface of the first substrate 21, the term "above" refers to a direction from the first substrate 21 toward the photodiode PD, and the term "below" refers to a direction from the photodiode PD toward the first substrate 21. The term "plan view" refers to a case of viewing from the direction orthogonal to the surface of the first substrate 21.

As illustrated in FIG. 6, the partial detection area PAA is an area surrounded by the first gate lines GCL and the signals line SGL. In the present embodiment, the first gate line GCL includes a lower gate line GCLa and an upper gate line GCLb. The lower gate line GCLa is provided so as to overlap the upper gate line GCLb. The lower gate line GCLa and the upper gate line GCLb are provided in different layers with insulating layers (a third inorganic insulating layer 22c and a fourth inorganic insulating layer 22d (refer to FIG. 8)) interposed therebetween. The lower gate line GCLa and the upper gate line GCLb are electrically coupled to each other at any place and are supplied with the gate drive signals Vgcl having the same potential. At least one of the lower gate line GCLa and the upper gate line GCLb is coupled to the gate line drive circuit 15. Although FIG. 6 illustrates the lower gate line GCLa and the upper gate line GCLb with different widths for ease of viewing, the lower and the upper gate lines GCLa and GCLb may have the same width.

The partial detection area PAA includes the first switching element Tr, a first conductive layer 65, a second conductive layer 66, a third conductive layer 67, and a fourth conductive layer 68. The first switching element Tr is provided near an intersecting portion between the first gate line GCL and the signal line SGL. The first switching element Tr includes a first semiconductor 61, a source electrode 62, a drain electrode 63, a first gate electrode 64A, and a second gate electrode 64B.

The first semiconductor 61 is an oxide semiconductor. The first semiconductor 61 is more preferably a transparent amorphous oxide semiconductor (TAOS) among types of the oxide semiconductor. Using the oxide semiconductor as the first switching element Tr can reduce a leak current of the first switching element Tr.

The first semiconductor 61 is provided along the first direction Dx and intersects the first gate electrode 64A and the second gate electrode 64B in the plan view. The first gate electrode 64A and the second gate electrode 64B are provided so as to branch from the lower gate line GCLa and the upper gate line GCLb, respectively. In other words, portions of the lower gate line GCLa and the upper gate line GCLb overlapping the first semiconductor 61 serve as the first gate electrode 64A and the second gate electrode 64B, respectively. Aluminum (Al), copper (Cu), silver (Ag), molybdenum (Mo), or an alloy of these materials is used as the first gate electrode 64A and the second gate electrode 64B. A channel region is formed at a portion of the first semiconductor 61 overlapping the first gate electrode 64A and the second gate electrode 64B.

One end of the first semiconductor 61 is coupled to the source electrode 62 through a contact hole H1. The other end of the first semiconductor 61 is coupled to the drain electrode 63 through a contact hole H2. A portion of the signal line SGL overlapping the first semiconductor 61 serves as the source electrode 62. A portion of the third conductive layer 67 overlapping the first semiconductor 61 serves as the drain electrode 63. The third conductive layer 67 is coupled to a lower electrode 35 of the photodiode PD through a contact hole H3 illustrated in FIG. 7. The above-described configuration allows the first switching element Tr to switch between coupling and uncoupling of the photodiode PD to and from the signal line SGL.

The first conductive layer 65 is provided so as to overlap the one end of the first semiconductor 61. The second conductive layer 66, the third conductive layer 67, and the fourth conductive layer 68 are provided so as to at least partially overlap with one another, and are provided in an area overlapping the photodiode PD. The fourth conductive layer 68 is coupled to the fourth conductive layer 68 of the partial detection area PAA adjacent in the first direction Dx through a coupling portion 68s.

As illustrated in FIG. 7, the photodiode PD is provided in an area surrounded by the first gate lines GCL and the signals line SGL. The photodiode PD includes a third semiconductor 31, an upper electrode 34, and the lower electrode 35. The photodiode PD is, for example, a positive-intrinsic-negative (PIN) photodiode.

A power supply signal line Lvs extends in the second direction Dy so as to overlap the signal line SGL. The upper electrode 34 is coupled to the power supply signal line Lvs through coupling wiring 36. The power supply signal line Lvs is wiring that supplies a power supply signal VDDSVS to the photodiode PD. The partial detection areas PAA arranged in the second direction Dy are coupled to the common power supply signal line Lvs. Since the power supply signal line Lvs overlaps the signal line SGL, the partial detection area PAA can have a larger opening.

Specifically, as illustrated in FIG. 8, the photodiode PD is provided on a first organic insulating layer 23a of the backplane 2 such that the lower electrode 35, the third semiconductor 31, and the upper electrode 34 are stacked thereon in the order as listed. The backplane 2 is a drive circuit board that drives a sensor for each predetermined detection area (each of the partial detection areas PAA or each of the detection area groups PAG). The backplane 2 includes the first substrate 21, and the first switching element Tr, the fifth switching element TrG, and various types of wiring provided on the first substrate 21.

The third semiconductor 31 is of amorphous silicon (a-Si). Alternatively, the third semiconductor 31 may be of polysilicon, and more preferably, may be of low-temperature polysilicon (hereinafter, referred to as low-temperature polycrystalline silicon (LTPS)). The third semiconductor 31 includes an i-type semiconductor 32a, a p-type semiconductor 32b, and an n-type semiconductor 32c. The i-type semiconductor 32a, the p-type semiconductor 32b, and the n-type semiconductor 32c are a specific example of a photoelectric conversion element. In FIG. 8, the n-type semiconductor 32c, the i-type semiconductor 32a, and the p-type semiconductor 32b are stacked in the direction orthogonal to the surface of the first substrate 21 in the order as listed. However, a reversed configuration may be employed. That is, the p-type semiconductor 32b, the i-type semiconductor 32a, and the n-type semiconductor 32c may be stacked in the order as listed.

The a-Si of the n-type semiconductor 32c is doped with impurities to form an n+ region. The a-Si of the p-type semiconductor 32b is doped with impurities to form a p+ region. The i-type semiconductor 32a is, for example, a non-doped intrinsic semiconductor or a low-impurity region, and has lower conductivity than that of the n-type semiconductor 32c and the p-type semiconductor 32b.

The lower electrode 35 is the cathode of the photodiode PD and is an electrode for reading the detection signal Vdet. For example, a metal material such as titanium (Ti) is used as the lower electrode 35. The lower electrode 35 may be of a light-transmitting conductive material such as indium tin oxide (ITO). Alternatively, the lower electrode 35 may be a multilayered film having a plurality of stacked layers of, for example, a plurality of different metal materials and ITO.

The upper electrode 34 is the anode of the photodiode PD, and is an electrode for supplying the sensor power supply signal VDDSNS to a photoelectric conversion layer. The upper electrode 34 is a light-transmitting conductive layer of, for example, ITO. A plurality of the upper electrodes 34 are provided for each of the photodiodes PD.

As illustrated in FIG. 8, a sixth inorganic insulating layer 22f and a seventh inorganic insulating layer 22g are provided on the first organic insulating layer 23a. The sixth inorganic insulating layer 22f covers a peripheral portion of the upper electrode 34 and is provided with an opening in a position overlapping the upper electrode 34. The coupling wiring 36 is coupled to the upper electrode 34 at a portion of the upper electrode 34 not provided with the sixth inorganic insulating layer 22f. The seventh inorganic insulating layer 22g is provided on the sixth inorganic insulating layer 22f so as to cover the upper electrode 34 and the coupling wiring 36. A second organic insulating layer 23b serving as a planarizing layer is provided on the seventh inorganic insulating layer 22g. An opening H7 is provided in the sixth inorganic insulating layer 22f and the seventh inorganic insulating layer 22g at a position not overlapping the lower electrode 35. This configuration allows the fingerprint detection device 1 to let out water contained in the first organic insulating layer 23a through the opening H7.

The following describes a layer configuration of the first switching element Tr. As illustrated in FIG. 8, the first switching element Tr is provided on the first substrate 21. The first substrate 21 is, for example, a glass substrate. Alternatively, the first substrate 21 may be a resin substrate or a resin film formed of a resin such as polyimide.

A first inorganic insulating layer 22a, a second inorganic insulating layer 22b, the second gate electrode 64B, the third inorganic insulating layer 22c, the first semiconductor 61, the fourth inorganic insulating layer 22d, the first gate electrode 64A, a fifth inorganic insulating layer 22e, the source electrode 62 (signal line SGL), and the drain electrode 63 (third conductive layer 67) are stacked on the first substrate 21 in the order as listed.

For example, a silicon oxide (SiO) film, a silicon nitride (SiN) film, or a silicon oxynitride (SiON) film is used as each of the first to the seventh inorganic insulating layers 22a to 22g. Each of the inorganic insulating layers is not limited to a single layer and may be a multilayered film.

The first conductive layer 65 and the second conductive layer 66 are provided on the third inorganic insulating layer 22c. The first conductive layer 65 is provided so as to cover an end of the first semiconductor 61 that is a portion coupled to the source electrode 62. The second conductive layer 66 is provided so as to cover an end of the first semiconductor 61 that is a portion coupled to the drain electrode 63.

The first semiconductor 61 is provided between the first gate electrode 64A and the second gate electrode 64B in the direction orthogonal to the first substrate 21. That is, the first switching element Tr has what is called a dual-gate structure. However, the first switching element Tr may have a top-gate structure in which the first gate electrode 64A is provided while the second gate electrode 64B is not provided, or a bottom-gate structure in which only the second gate electrode 64B is provided without the first gate electrode 64A being provided.

The drain electrode 63 is the third conductive layer 67 provided above the first semiconductor 61. The fourth inorganic insulating layer 22d and the fifth inorganic insulating layer 22e are each provided with the contact hole H1 and the contact hole H2. The first conductive layer 65 is exposed at the bottom of the contact hole H1. The source electrode 62 is electrically coupled to the first semiconductor 61 through the contact hole H1 and the first conductive layer 65. In the same manner, the second conductive layer 66 is exposed at the bottom of the contact hole H2. The drain electrode 63 is electrically coupled to the first semiconductor 61 through the contact hole H2 and the second conductive layer 66.

Since the first conductive layer 65 and the second conductive layer 66 are provided in the fingerprint detection device 1, the first semiconductor 61 can be restrained from being removed by an etching liquid when the contact holes H1 and H2 are formed by etching. That is, in the fingerprint detection device 1, the first switching elements Tr in the detection area AA and the fifth switching elements TrG in the peripheral area GA can be formed in the same process, so that the manufacturing cost can be reduced.

A metal material such as aluminum (Al), copper (Cu), silver (Ag), or molybdenum (Mo), or an alloy of these materials is used as the first conductive layer 65, the second conductive layer 66, and the third conductive layer 67. The first conductive layer 65 and the second conductive layer 66 only need to be made of a conductive material that restrains the etching from progressing when the contact holes H1 and H2 are formed.

The third conductive layer 67 is provided in an area overlapping the photodiode PD in the plan view. The third conductive layer 67 is also provided above the first semiconductor 61, the first gate electrode 64A, and the second gate electrode 64B. That is, the third conductive layer 67 is provided between the first gate electrode 64A and the lower electrode 35 in the direction orthogonal to the first substrate 21. This configuration causes the third conductive layer 67 to have a function as a protection layer protecting the first switching element Tr.

The second conductive layer 66 extends so as to face the third conductive layer 67 in an area not overlapping the first semiconductor 61. The fourth conductive layer 68 is provided above the fourth inorganic insulating layer 22d in an area not overlapping the first semiconductor 61. The fourth conductive layer 68 is provided between the second conductive layer 66 and the third conductive layer 67. This configuration forms a capacitance between the second conductive layer 66 and the fourth conductive layer 68, and between the third conductive layer 67 and the fourth conductive layer 68. The capacitances formed by the second conductive layer 66, the third conductive layer 67, and the fourth conductive layer 68 serve as a capacitance of the capacitive element Ca illustrated in FIG. 5. Barrier layers 68a and 64Aa are provided at the lower part of the fourth conductive layer 68 and at the lower part of the first gate electrode 64A, respectively. The barrier layers 68a and 64Aa are formed of an oxide such as aluminum oxide.

The first organic insulating layer 23a is provided on the upper side of the fifth inorganic insulating layer 22e so as to cover the source electrode 62 (signal line SGL) and the drain electrode 63 (third conductive layer 67). The first organic insulating layer 23a is a planarizing layer that planarizes asperities formed by the first switching element Tr and various types of conductive layers. The lower electrode 35 is electrically coupled to the third conductive layer 67 through the contact hole H3 provided in the first organic insulating layer 23a. That is, the third conductive layer 67 is electrically coupled to the lower electrode 35 serving as the cathode of the photodiode PD and is provided between the photodiode PD and the first gate electrode 64A of the first switching element Tr.

The peripheral area GA is provided with the fifth switching element TrG of the gate line drive circuit 15. The fifth switching element TrG is provided on the same first substrate 21 as that of the first switching element Tr. The fifth switching element TrG includes the second semiconductor 81, a source electrode 82, a drain electrode 83, and a gate electrode 84. The first inorganic insulating layer 22a, the second semiconductor 81, the second inorganic insulating layer 22b, the gate electrode 84, the third inorganic insulating layer 22c, the fourth inorganic insulating layer 22d, the fifth inorganic insulating layer 22e, the source electrode 82, and the drain electrode 83 are stacked on the first substrate 21 in the order as listed.

The second semiconductor 81 is of polysilicon. The second semiconductor 81 is more preferably of LTPS. The fifth switching element TrG using LTPS can be produced at a process temperature of 600 degrees Celsius or lower. Therefore, circuits such as the gate line drive circuit 15 and the signal line selection circuit 16 can be formed on the same substrate as that of the first switching element Tr. Polysilicon has higher carrier mobility than that of a-Si. Therefore, the fingerprint detection device 1 can reduce the size of the gate line drive circuit 15 by using polysilicon as the fifth switching element TrG. As a result, in the fingerprint detection device 1, the peripheral area GA can be smaller. The fifth switching element TrG using polysilicon has higher reliability than that obtained using a-Si.

The first semiconductor 61 of the first switching element Tr is provided in a position further away from the first substrate 21 than the second semiconductor 81 of the fifth switching element TrG in the direction orthogonal to the first substrate 21. This configuration allows the second semiconductor 81 formed of polysilicon and the first semiconductor 61 formed of an oxide semiconductor to be formed on the same first substrate 21.

The gate electrode 84 is provided in the same layer as that of the second gate electrode 64B. The fifth switching element TrG has what is called the top-gate structure. However, the fifth switching element TrG may have the dual-gate structure or the bottom-gate structure.

The source electrode 82 and the drain electrode 83 are provided in the same layer as that of the source electrode 62 and the drain electrode 63 of the first switching element Tr. Contact holes H4 and H5 are provided through from the second inorganic insulating layer 22b to the fifth inorganic insulating layer 22e. The source electrode 82 is electrically coupled to the second semiconductor 81 through the contact hole H4. The drain electrode 83 is electrically coupled to the second semiconductor 81 through the contact hole H5.

The terminal portion 72 is provided in a position of the peripheral area GA different from the area provided with the gate line drive circuit 15. The terminal portion 72 includes a first terminal conductive layer 73, a second terminal conductive layer 74, a third terminal conductive layer 75, and a fourth terminal conductive layer 76. The first terminal conductive layer 73 is provided in the same layer as that of the second gate electrode 64B on the second inorganic insulating layer 22b. A contact hole H6 is provided so as to communicate through the third inorganic insulating layer 22c, the fourth inorganic insulating layer 22d, the fifth inorganic insulating layer 22e, and the first organic insulating layer 23a.

The second terminal conductive layer 74, the third terminal conductive layer 75, and the fourth terminal conductive layer 76 are stacked in the contact hole H6 in the order as listed, and are electrically coupled to the first terminal conductive layer 73. The second terminal conductive layer 74 can be formed with the same material and in the same process as the third conductive layer 67 and the like. The third terminal conductive layer 75 can be formed with the same material and in the same process as the lower electrode 35. The fourth terminal conductive layer 76 is formed with the same material and in the same process as the coupling wiring 36 and the power supply signal line Lvs (refer to FIG. 7).

Although FIG. 8 illustrates the one terminal portion 72, a plurality of such terminal portions 72 are arranged with gaps interposed therebetween. The terminal portions 72 are electrically coupled to the flexible printed circuit board 71 (refer to FIG. 2) through, for example, an anisotropic conductive film (ACF).

Figure 9:
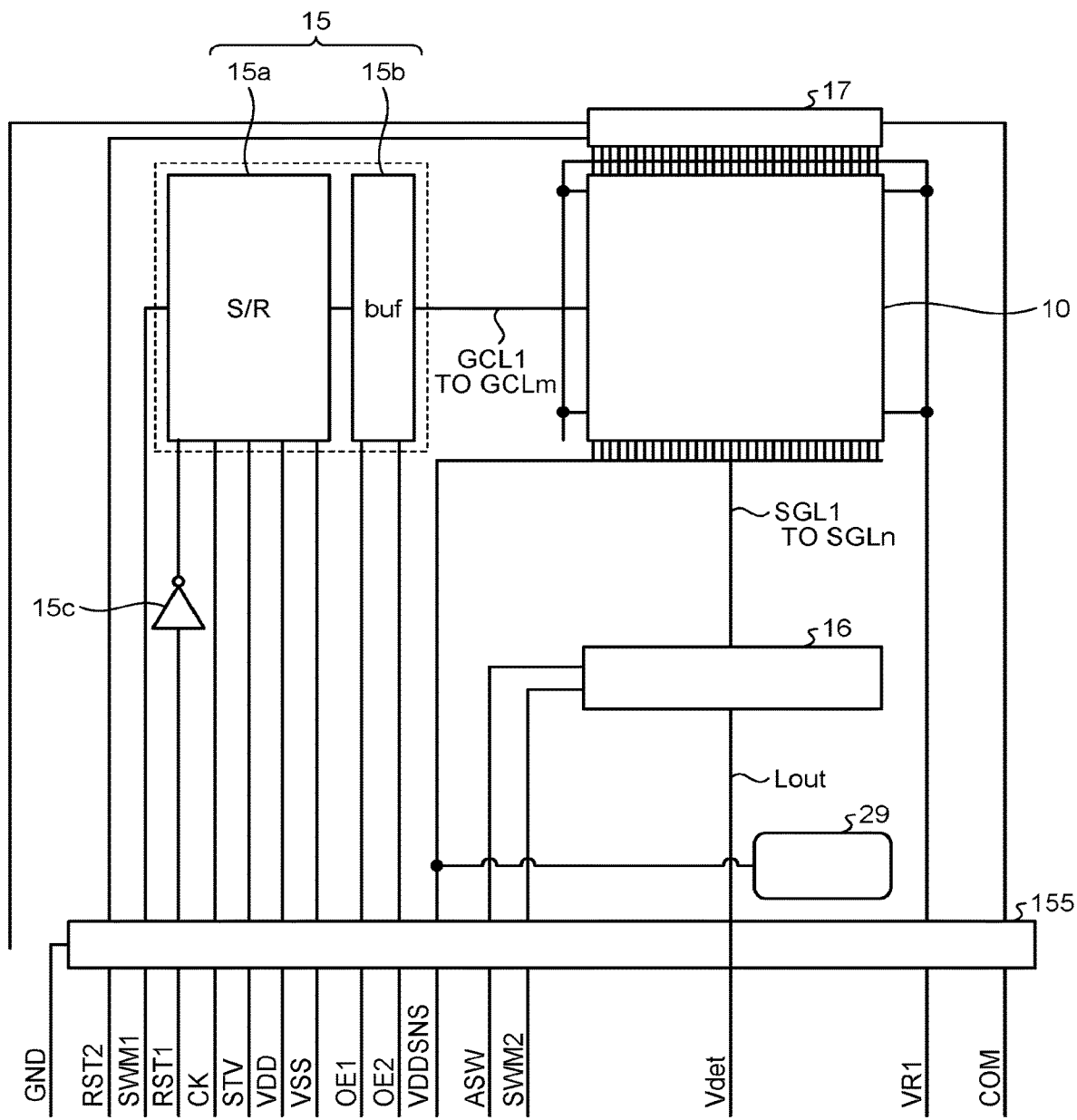
FIG. 9 is a block diagram illustrating a configuration example of a sensor, a gate line drive circuit, and a signal line selection circuit.
Figure 10:
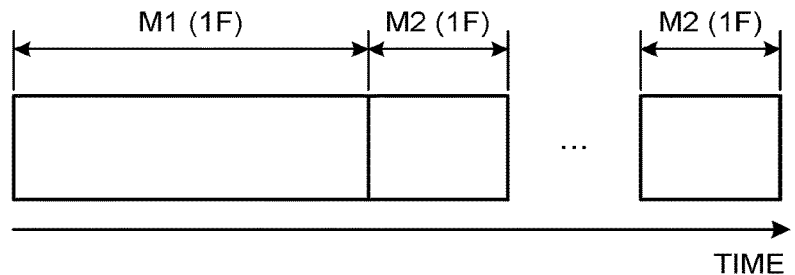
FIG. 10 is an explanatory diagram for explaining a relation of a first detection mode and a second detection mode with time.
Figure 11:
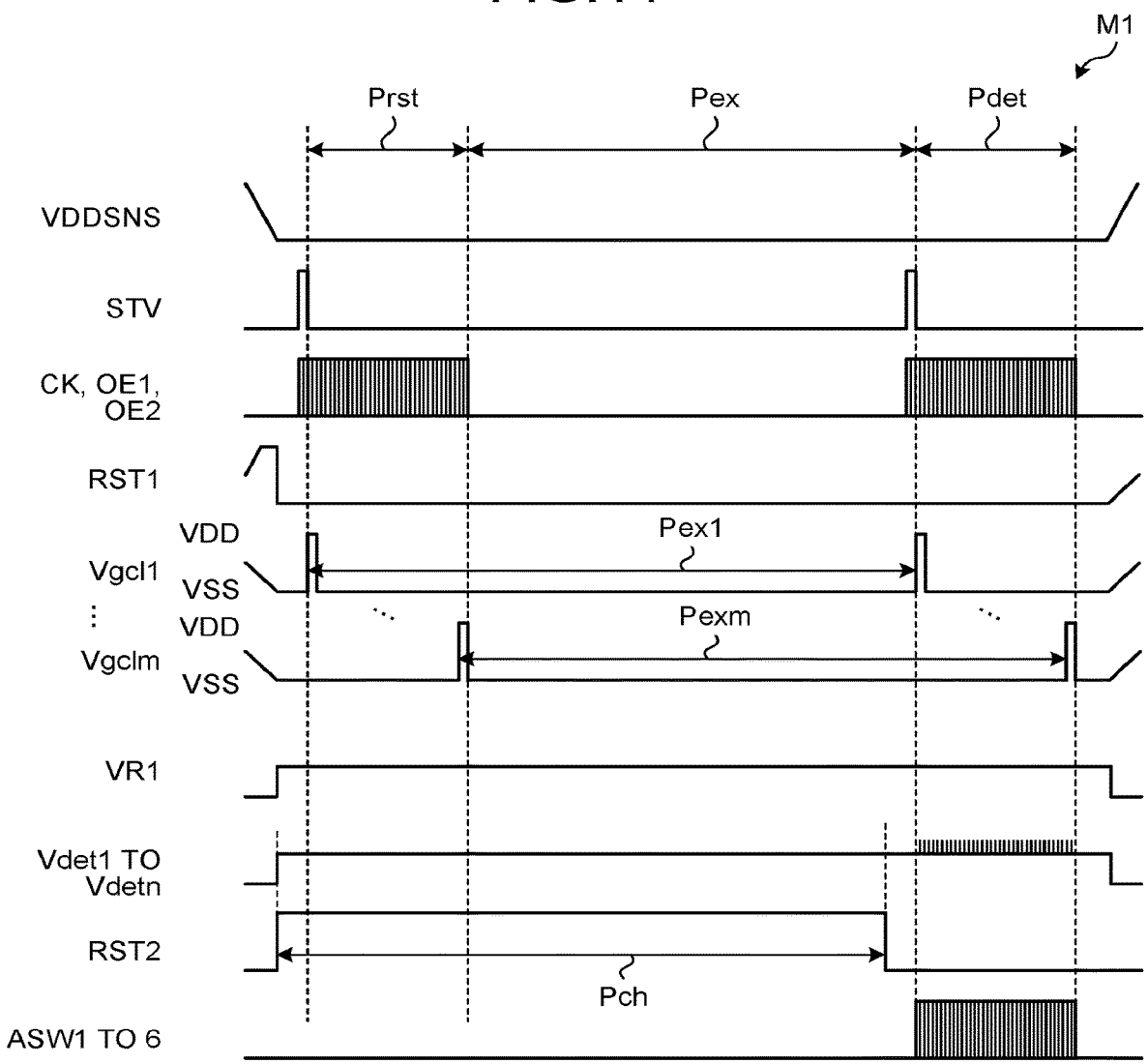
FIG. 11 is a timing waveform diagram illustrating an operation example of the fingerprint detection device.
Figure 12:
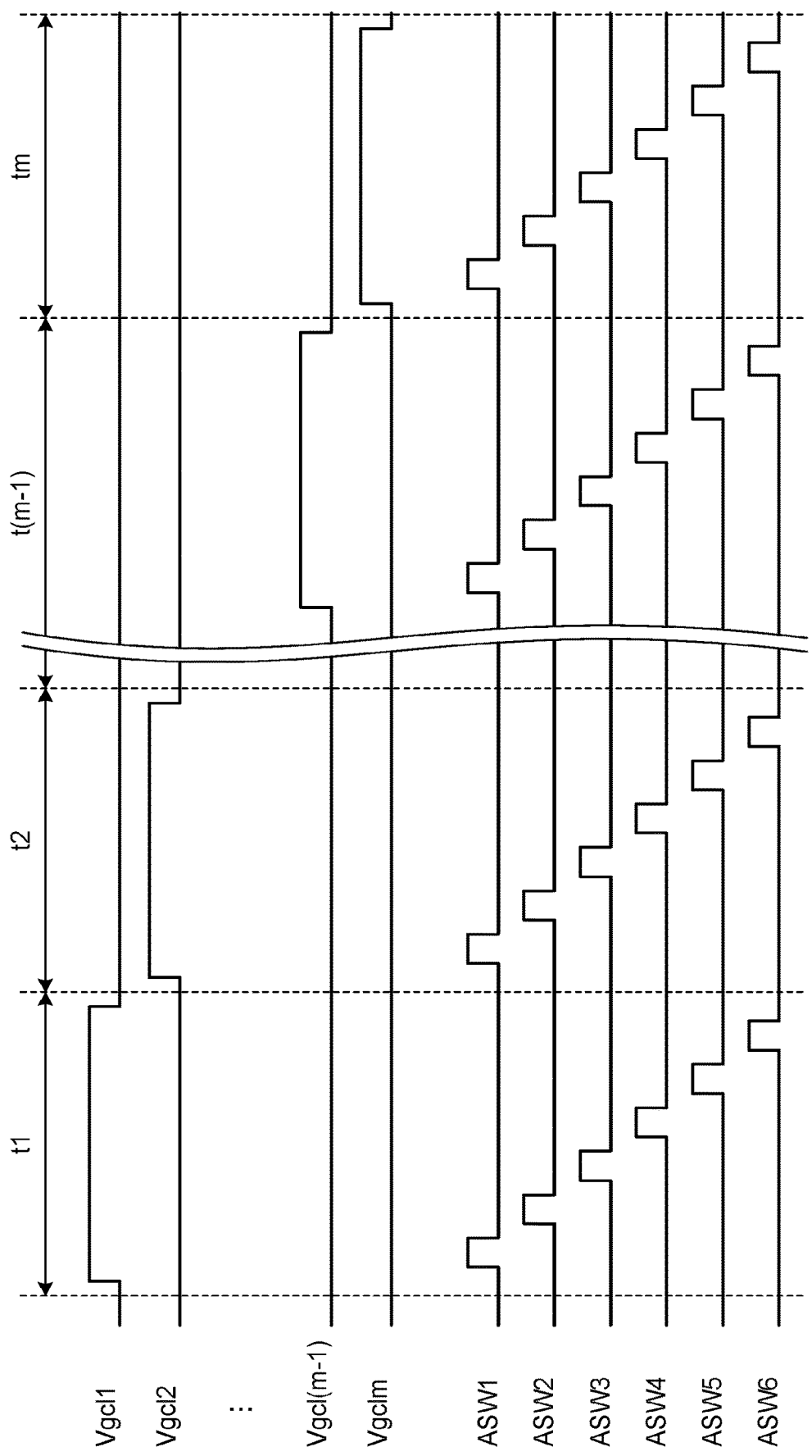
FIG. 12 is a timing waveform diagram illustrating an operation example during a reading period in the first detection mode.
Figure 13:
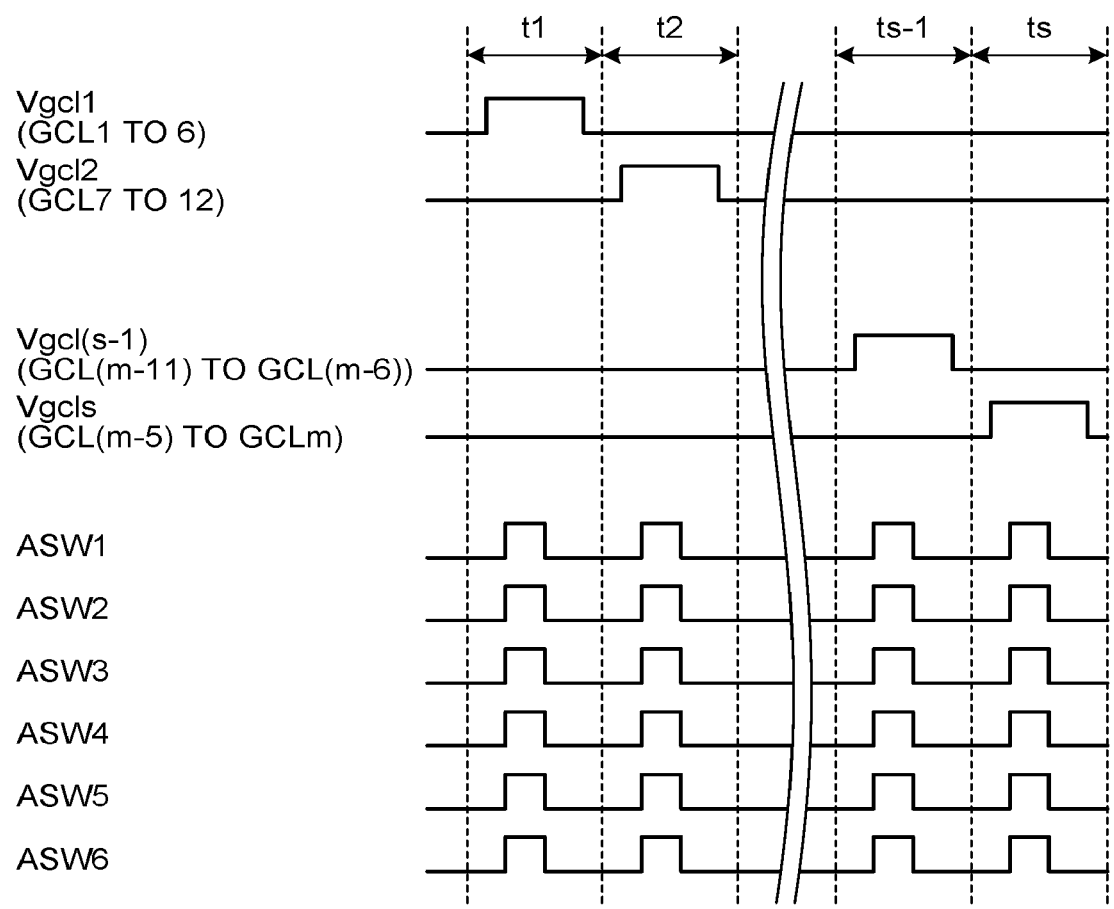
FIG. 13 is a timing waveform diagram illustrating an operation example during the reading period in the second detection mode.

The following describes an operation example of the fingerprint detection device 1. FIG. 9 is a block diagram illustrating a configuration example of the sensor, the gate line drive circuit, and the signal line selection circuit. FIG. 10 is an explanatory diagram for explaining a relation of the first detection mode and the second detection mode with time. FIG. 11 is a timing waveform diagram illustrating the operation example of the fingerprint detection device. FIG. 12 is a timing waveform diagram illustrating the operation example during a reading period in the first detection mode. FIG. 13 is a timing waveform diagram illustrating the operation example during the reading period in the second detection mode.

As illustrated in FIG. 9, the fingerprint detection device 1 further includes an inverter 15c, a protection circuit 155, and a terminal 29. The protection circuit 155 includes protection resistor elements and protection diodes. Various signals supplied from the control board 121 (refer to FIG. 2) are supplied through the protection circuit 155 to the gate line drive circuit 15, the signal line selection circuit 16, and the reset circuit 17. The output signal lines Lout of the signal line selection circuit 16 are coupled to the detection circuit 48 without passing through the protection diodes of the protection circuit 155. This configuration can hamper a reduction in intensity of signals output from the sensor 10.

The gate line drive circuit 15 includes a shift register 15a and a buffer circuit 15b. The inverter 15c receives the reset signal RST1 from the control circuit 122 and outputs an inverted reset signal to the shift register 15a. The inverted reset signal is a voltage signal obtained by inverting the reset signal RST1. The shift register 15a sequentially outputs an output signal to the buffer circuit 15b based on the reset signal RST1, a clock signal CK, the start signal STV, and power supply voltages VDD and VSS supplied from the external control circuit 122. The buffer circuit 15b receives the output signal from the shift register 15a, and generates the gate drive signals Vgcl in response to control signals OE1 and OE2 and based on the power supply voltages VDD and VSS. The buffer circuit 15b supplies the gate drive signals Vgcl to the first gate lines GCL.

The gate line drive circuit 15 and the signal line selection circuit 16 switch between the first detection mode M1 and the second detection mode M2 based on switching control signals SWM1 and SWM2.

As illustrated in FIG. 10, the fingerprint detection device 1 performs the detection for a detection frame (1F) in the first detection mode M1, and then, repeatedly performs the detection for the detection frame (1F) in the second detection mode M2 a plurality of times. The detection frame (1F) corresponds to an area overlapping the entire detection area AA, that is, an area in which a detection target object such as the finger Fg can be detected by driving all the first gate lines GCL. However, there may be a case where the detection for the detection frame (1F) is performed in a partial area of the detection area AA.

In the second detection mode M2, the detection is performed at a larger detection pitch than that in the first detection mode M1. As a result, the period required for the detection for one detection frame (1F) can be reduced. By repeatedly performing the detection in the second detection mode M2, the fingerprint detection device 1 can increase the detection accuracy in the second detection mode M2 and can detect a change in the detection target object with time. Specifically, the fingerprint detection device 1 can detect the biological information, such as the pulsation, based on the change in the blood vessel image in the finger Fg with time.

The fingerprint detection device 1 may perform the first detection mode M1 and the second detection mode M2 in any manner. For example, the fingerprint detection device 1 may repeatedly perform the detection in the first detection mode M1 for a plurality of the detection frames (1F). The fingerprint detection device 1 may perform the second detection mode M2, and then, repeatedly perform the first detection mode M1.

As illustrated in FIG. 11, the fingerprint detection device 1 includes a reset period Prst, an exposure period Pex, and a reading period Pdet. The power supply circuit 123 supplies the sensor power supply signal VDDSNS to the anode of the photodiode PD through the reset period Prst, the exposure period Pex, and the reading period Pdet. The control circuit 122 supplies the reference signal VR1 and the reset signal RST2 serving as high-level voltage signals to the reset circuit 17 from a time before the reset period Prst starts. The control circuit 122 supplies the start signal STV to the gate line drive circuit 15, and the reset period Prst starts.

During the reset period Prst, the shift register 15a included in the gate line drive circuit 15 sequentially selects each of the first gate lines GCL based on the start signal STV, the clock signal CK, and the reset signal RST1. The gate line drive circuit 15 sequentially supplies the gate drive signal Vgcl to each of the first gate lines GCL. The gate drive signal Vgcl has a pulsed waveform having the power supply voltage VDD serving as a high-level voltage and the power supply voltage VSS serving as a low-level voltage. In FIG. 11, m first gate lines GCL (where m is, for example, 256) are provided, and gate drive signals Vgcl1, ..., Vgclm are sequentially supplied to the first gate lines GCL.

Thus, during the reset period Prst, the capacitive elements Ca of all the partial detection areas PAA are sequentially electrically coupled to the signal lines SGL and are supplied with the reference signal VR1. As a result, the capacitance of the capacitive elements Ca are reset.

After the gate drive signal Vgcl is supplied to the first gate line GCL, the exposure period Pex starts. The start timing and end timing of actual exposure periods Pex1, ..., Pexm in the partial detection areas PAA corresponding to the first gate lines GCL differ from one another. Each of exposure periods Pex1, ..., Pexm starts at a time when the gate drive signal Vgcl changes from the power supply voltage VDD serving as the high-level voltage to the power supply voltage VSS serving as the low-level voltage during the reset period Prst. Each of exposure periods Pex1, ..., Pexm ends at a time when the gate drive signal Vgcl changes from the power supply voltage VSS to the power supply voltage VDD during the reading period Pdet. The lengths of exposure time of the exposure periods Pex1, ..., Pexm are equal to one another.

During the exposure period Pex, the current corresponding to the light irradiating the photodiode PD flows in each of the partial detection areas PAA. As a result, the electrical charge is stored in each of the capacitive elements Ca.

At a time before the reading period Pdet starts, the control circuit 122 sets the reset signal RST2 to a low-level voltage. This operation stops the reset circuit 17 from operating. During the reading period Pdet, the gate line drive circuit 15 sequentially supplies the gate drive signals Vgcl1, ..., Vgclm to the first gate lines GCL in the same manner as during the reset period Prst.

Specifically, in the first detection mode M1, as illustrated in FIG. 12, the gate line drive circuit 15 supplies the gate drive signal Vgcl1 at the high-level voltage (power supply voltage VDD) to the first gate line GCL1 during a period t1. The control circuit 122 sequentially supplies selection signals ASW1, ..., ASW6 to the signal line selection circuit 16 during a period in which the gate drive signal Vgcl1 is at the high-level voltage (power supply voltage VDD). This operation sequentially or simultaneously couples the signal lines SGL for the partial detection areas PAA selected by the gate drive signal Vgcl1 to the detection circuit 48. As a result, the detection signal Vdet for each of the partial detection areas PAA is supplied to the detection circuit 48.

In the same manner, the gate line drive circuit 15 supplies the gate drive signals Vgcl2, ..., Vgcl(m−1), Vgclm at the high-level voltage to first gate lines GCL2, ..., GCL(m−1), GCLm during periods t2, ..., t(m−1), tm, respectively. That is, in the first detection mode M1, the gate line drive circuit 15 supplies the gate drive signal Vgcl to a third number (where the third number is one in FIG. 12) of the first gate lines GCL during each of the periods t1, t2, ..., t(m−1), tm. The signal line selection circuit 16 sequentially selects each of the signal lines SGL based on the selection signal ASW during each period in which the gate drive signal Vgcl is set to the high-level voltage. In the first detection mode M1, the signal line selection circuit 16 sequentially couples the signal lines SGL to the one detection circuit 48 in units of a first number (where the first number is one in FIG. 12) of the signal lines SGL. Thus, the fingerprint detection device 1 can output the detection signals Vdet of all the partial detection areas PAA to the detection circuit 48 during the reading period Pdet.

As illustrated in FIG. 13, in the second detection mode M2, the gate line drive circuit 15 supplies the gate drive signal Vgcl1 at the high-level voltage (power supply voltage VDD) to the first gate lines GCL1 to GCL6 during the period t1. The control circuit 122 simultaneously supplies the selection signals ASW1, . . . , ASW6 to the signal line selection circuit 16 during the period in which the gate drive signal Vgcl1 is at the high-level voltage (power supply voltage VDD). This operation causes the signal line selection circuit 16 to simultaneously couple a second number, larger than the first number (where the second number is six in FIG. 13), of the signal lines SGL to the detection circuit 48 in the second detection mode M2. As a result, each of the detection signals Vdet of the detection area groups PAG1 and PAG2 (refer to FIG. 4) is supplied to the detection circuit 48.

In the same manner, the gate line drive circuit 15 supplies the gate drive signals Vgcl2, . . . , Vgcl(s−1), Vgcls at the high-level voltage during the periods t2, . . . , t(s−1), ts, respectively, to the first gate lines GCL7 to GCL12, . . . , the first gate lines GCL(m−11) to GCL(m−6), and the first gate lines GCL(m−5) to GCLm. That is, in the second detection mode M2, the gate line drive circuit 15 simultaneously supplies the gate drive signal Vgcl to a fourth number (different from the third number) (where the fourth number is six in FIG. 13) of the first gate lines GCL during each of the periods t1, t2, . . . , t(s−1), ts.

This operation allows the fingerprint detection device 1 to output the detection signals Vdet to the detection circuit 48 for each of the detection area groups PAG during the reading period Pdet. Thus, the fingerprint detection device 1 can increase a signal-to-noise (S/N) ratio in the detection in the second detection mode M2 to be higher than in the case of performing the detection for each of the partial detection areas PAA.

Although FIG. 13 illustrates the example in which the gate line drive circuit 15 drives six of the first gate lines GCL in a bundle in the second detection mode M2, the driving method is not limited thereto. The gate line drive circuit 15 may drive five or less of the first gate lines GCL in a bundle, or may drive seven or more of the first gate lines GCL in a bundle. The signal line selection circuit 16 may simultaneously couple five or less of the signal lines SGL to the detection circuit 48, or may simultaneously couple seven or more of the signal lines SGL to the detection circuit 48.

The fingerprint detection device 1 may perform the fingerprint detection by repeatedly performing the processing during the reset period Prst, the processing during the exposure period Pex, and the processing during the reading period Pdet. Alternatively, the fingerprint detection device 1 may start the detection operation when the touchscreen panel 102 has detected that, for example, the finger Fg is in contact with or in proximity to the detection surface.

Although FIGS. 11 and 12 illustrate the case where the gate line drive circuit 15 sequentially supplies the gate drive signals Vgcl to the first gate lines GCL in the first detection mode M1, the driving method is not limited to this case. The sensor 10 may perform code division selection driving (hereinafter, called "code division multiplexing (CDM) driving") to perform the detection in the first detection mode M1. That is, in the CDM driving, the gate line drive circuit 15 may supply the gate drive signals Vgcl to each of the groups of the first gate lines GCL, which are different from each other, for the respective periods t, t1, . . . , t(m−1), tm based on a predetermined code. The detector 40 decodes the detection signals Vdet for each of the periods to calculate the detection signal for each of the partial detection areas PAA.

As described above, the fingerprint detection device 1 of the present embodiment includes the first substrate 21, the photoelectric conversion elements (photodiodes PD) that are provided to the first substrate 21 and each output the signal corresponding to the light emitted thereto, the signal lines SGL coupled to the photoelectric conversion elements, the detection circuit 48 electrically coupled to the photoelectric conversion elements through the signal lines SGL, the signal line selection circuit 16 that switches the number of the signal lines SGL to be coupled to the one detection circuit 48.

The signal line selection circuit 16 couples the first number (for example, one) of the signal lines SGL to the one detection circuit 48 in the first detection mode M1 and couples the second number, larger than the first number (for example, six), of the signal lines SGL to the detection circuit 48 in the second detection mode M2 of detecting the light at the detection pitch different from that in the first detection mode M1.

With this configuration, the fingerprint detection device 1 can vary the resolution of detection in the first direction Dx between the first detection mode M1 and the second detection mode M2 by the operation of the signal line selection circuit 16. Specifically, in the first detection mode M1 of detecting the fingerprint, the fingerprint detection device 1 performs the detection at a smaller detection pitch for every partial detection area PAA, and in the second detection mode M2 of detecting the biological information such as the blood vessel image, the fingerprint detection device 1 performs the detection at a larger detection pitch than that in the first detection mode M1. Thus, the fingerprint detection device 1 can detect the fingerprint at a higher definition in the first detection mode M1, and can increase the S/N ratio to properly detect the biological information, such as the blood vessel image, in the second detection mode M2. In the second detection mode M2, the detection target can be detected quickly, so that a change in the blood vessel image with time, such as a pulse wave, can be properly detected.

The fingerprint detection device 1 also includes the first switching elements Tr each provided for a corresponding one of the photoelectric conversion elements, the first gate lines GCL each coupled to corresponding first switching elements Tr, and the gate line drive circuit 15 that supplies the gate drive signals Vgcl to the first gate lines GCL. The gate line drive circuit 15 supplies the gate drive signals Vgcl to the third number of the first gate lines GCL in the first detection mode M1, and simultaneously supplies the gate drive signals Vgcl to the fourth number (different from the third number) of the first gate lines GCL in the second detection mode M2.

With this configuration, the fingerprint detection device 1 can vary the resolution of detection in the second direction Dy between the first detection mode M1 and the second detection mode M2 by the operation of the gate line drive circuit 15. In the second detection mode M2, when the fingerprint detection device 1 performs different types of detection, such as the detection of the blood vessel image and the detection of the pulsation, the fingerprint detection device 1 may vary the resolution between the detection operations. In the detection of the pulsation, the fingerprint detection device 1 may perform the detection at a larger detection pitch than that in the detection of the blood vessel image.

By performing the first detection mode M1 and the second detection mode M2, the fingerprint detection device 1 can also determine, based on the biological information, whether the fingerprint detected in the first detection mode M1 is a forged fingerprint.

The configuration of the fingerprint detection device 1 can be changed as appropriate. For example, the configuration of the partial detection area PAA illustrated in FIGS. 6 to 8 is merely an example, and the planar shapes of the photodiode PD and the conductive layers and the layered structures of the switching elements can be changed as appropriate. For example, the first semiconductor 61 of the first switching element Tr and the second semiconductor 81 of the fifth switching element TrG may be fabricated from the same material.

Second Embodiment

Figure 14:
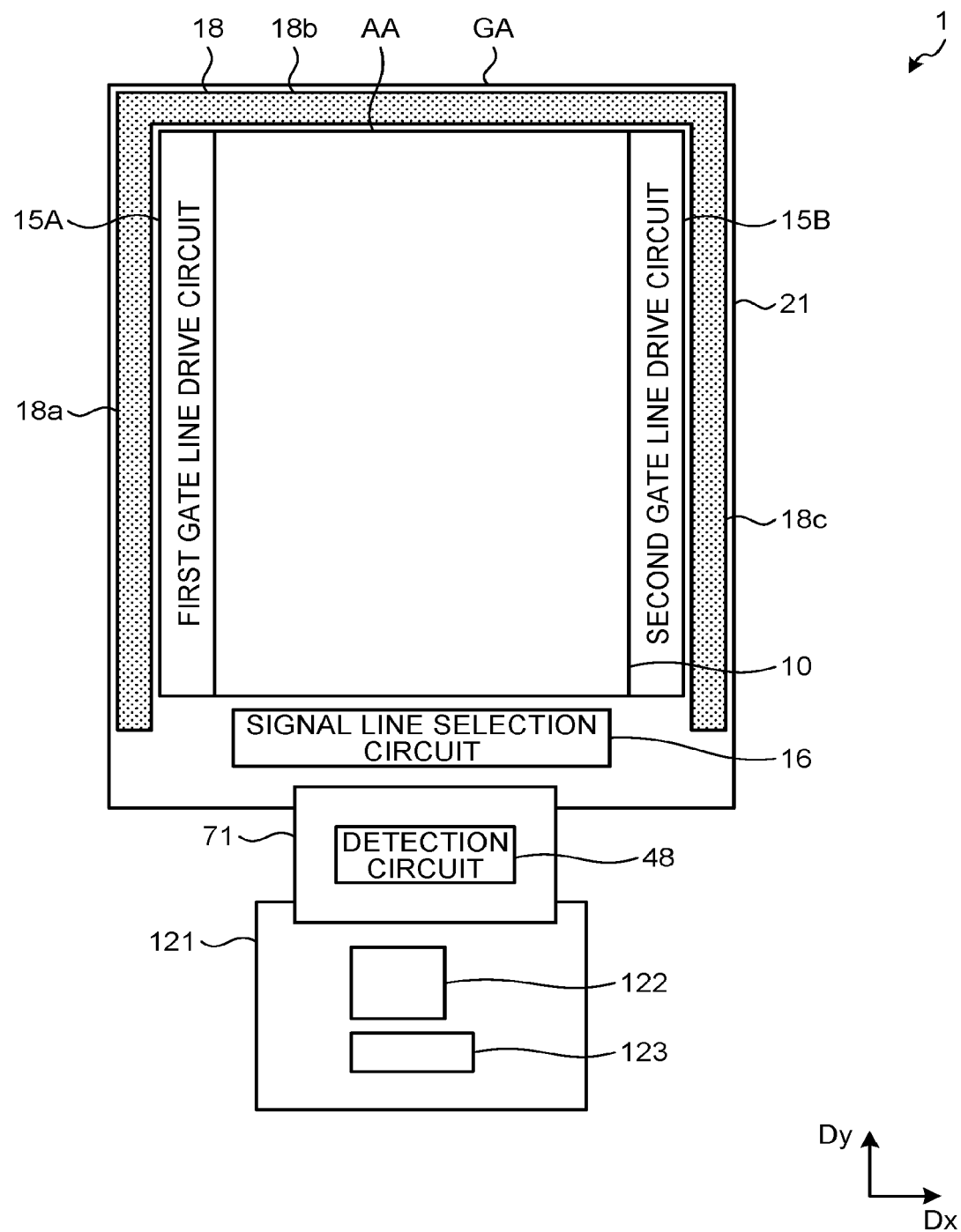
FIG. 14 is a plan view illustrating the fingerprint detection device according to a second embodiment.
Figure 15:
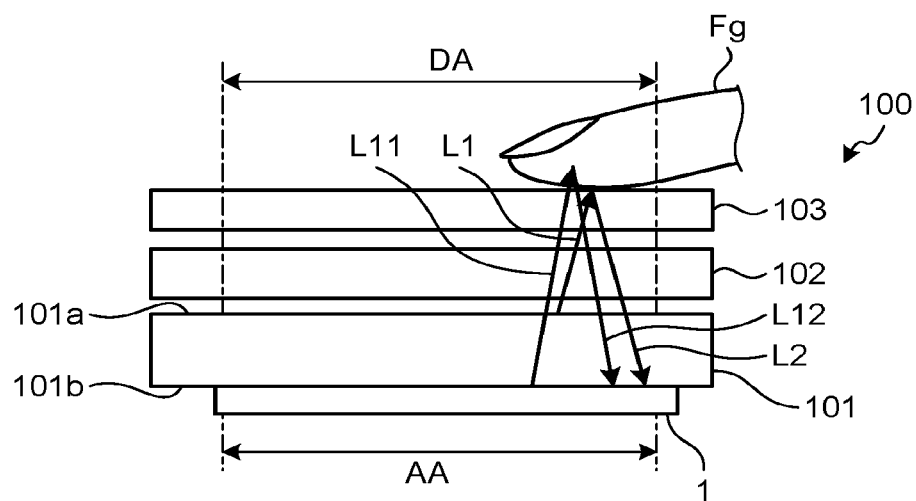
FIG. 15 is a sectional view illustrating a schematic sectional configuration of the display device with a fingerprint detection device according to the second embodiment.

FIG. 14 is a plan view illustrating the fingerprint detection device according to a second embodiment. FIG. 15 is a sectional view illustrating a schematic sectional configuration of the display device with a fingerprint detection device according to the second embodiment. In the following description, the components described in the above-described embodiment will be denoted by the same reference numerals, and will not be described.

As illustrated in FIG. 14, the fingerprint detection device 1 of the second embodiment includes a first gate line drive circuit 15A, a second gate line drive circuit 15B, and a light source 18. The first gate line drive circuit 15A is adjacent to the second gate line drive circuit 15B in the first direction Dx with the detection area AA interposed therebetween. The first gate line drive circuit 15A supplies the gate drive signal Vgcl to the third number (for example, one) of the first gate lines GCL in the first detection mode M1. The second gate line drive circuit 15B supplies the gate drive signal Vgcl to the fourth number (for example, six) of the first gate lines GCL in the second detection mode M2.

This configuration can vary the detection pitch (resolution) in the second direction Dy between the first detection mode M1 and the second detection mode M2 in the same manner as in the first embodiment. The first gate line drive circuit 15A and the second gate line drive circuit 15B are provided corresponding to the first detection mode M1 and the second detection mode M2, respectively, so that the circuit configuration can be simplified.

The light source 18 is provided in the peripheral area GA of the first substrate 21. The light source 18 includes a first light source 18a, a second light source 18b, and a third light source 18c, which are provided so as to surround three sides of the detection area AA. The first light source 18a is provided along the first gate line drive circuit 15A, between the first gate line drive circuit 15A and an end of the first substrate 21. The second light source 18b is provided in the peripheral area GA on a side opposite to the signal line selection circuit 16 side with the detection area AA interposed therebetween. The third light source 18c is provided along the second gate line drive circuit 15B, between the second gate line drive circuit 15B and an end of the first substrate 21.

The light source 18 emits, for example, near-infrared light (having a wavelength ranging at least from 840 nm to 850 nm) as invisible light. The light source 18 includes organic ELs (OLEDs). Alternatively, the light source 18 includes a plurality of inorganic light-emitting diodes (LEDs) being arrayed.

As illustrated in FIG. 15, in the first detection mode M1, the fingerprint detection device 1 detects the fingerprint using the light L1 that is visible light emitted from the display panel 101. Specifically, the fingerprint detection device 1 detects the light L2 obtained by reflecting the light L1 on the interface between the cover glass 103 and air and on the surface of the finger Fg.

In the second detection mode M2, the fingerprint detection device 1 detects the biological information using light L11 that is the near-infrared light emitted from the light source 18. Specifically, the fingerprint detection device 1 detects the light L12 obtained by reflecting the light L11 inside the finger Fg. Thus, the fingerprint detection device 1 detects the biological information on the finger Fg. Using the near-infrared light in the second detection mode M2 reduces the reflection and scattering on the surface of the finger Fg and can increase the S/N ratio in the second detection mode M2.

The arrangement of the light source 18 illustrated in FIG. 14 is merely an example, and can be changed as appropriate. There may be a case where one or some of the first light source 18a, the second light source 18b, and the third light source 18c are not provided.

First Modification of Second Embodiment

Figure 16:
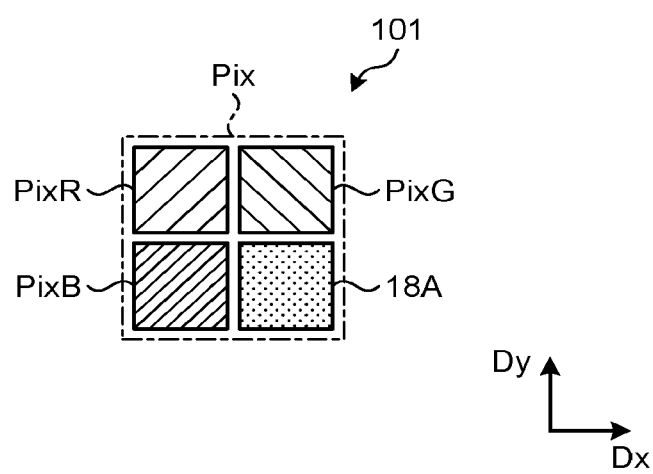
FIG. 16 is a plan view illustrating a configuration example of a pixel of the display device with a fingerprint detection device according to a first modification of the second embodiment.

FIG. 16 is a plan view illustrating a configuration example of a pixel of the display device with a fingerprint detection device according to a first modification of the second embodiment. Although the light source 18 is provided on the first substrate 21 in the second embodiment illustrated in FIGS. 14 and 15, the configuration is not limited thereto. A pixel Pix of the display panel 101 may include a light source 18A as illustrated in FIG. 16. The pixel Pix includes a red pixel PixR, a green pixel PixG, a blue pixel PixB, and the light source 18A. Each of the red pixel PixR, the green pixel PixG, the blue pixel PixB, and the light source 18A is formed of an OLED. The red pixel PixR emits red light. The green pixel PixG emits green light. The blue pixel PixB emits blue light. The light source 18A emits near-infrared light that is invisible light. As a result, the light from the light source 18A is restrained from degrading the display quality of the display panel 101.

The red pixel PixR and the green pixel PixG are arranged in the first direction Dx. The red pixel PixR and the blue pixel PixB are arranged in the second direction Dy. The light source 18A and the green pixel PixG are arranged in the second direction Dy. The light source 18A and the blue pixel PixB are arranged in the first direction Dx. The pixels Pix are arranged in a matrix having a row-column configuration in the display area DA of the display panel 101. The arrangement of the pixels and the light source 18A included in the pixel Pix is merely an example, and can be changed as appropriate. For example, the pixel Pix may include a plurality of pixels that emit light in four or more colors. The red pixel PixR, the green pixel PixG, the blue pixel PixB, and the light source 18A may be arranged in the first direction Dx.

In the first detection mode M1, the fingerprint detection device 1 detects the fingerprint using the light L1 that is the visible light emitted from at least one or more of the red pixel PixR, the green pixel PixG, and the blue pixel PixB of the display panel 101.

In the second detection mode M2, the fingerprint detection device 1 detects the biological information using the light L11 that is the near-infrared light emitted from the light source 18A of the display panel 101. The fingerprint detection device 1 can also properly detect the biological information when the light source 18A is provided on the display panel 101.

Third Embodiment

Figure 17:
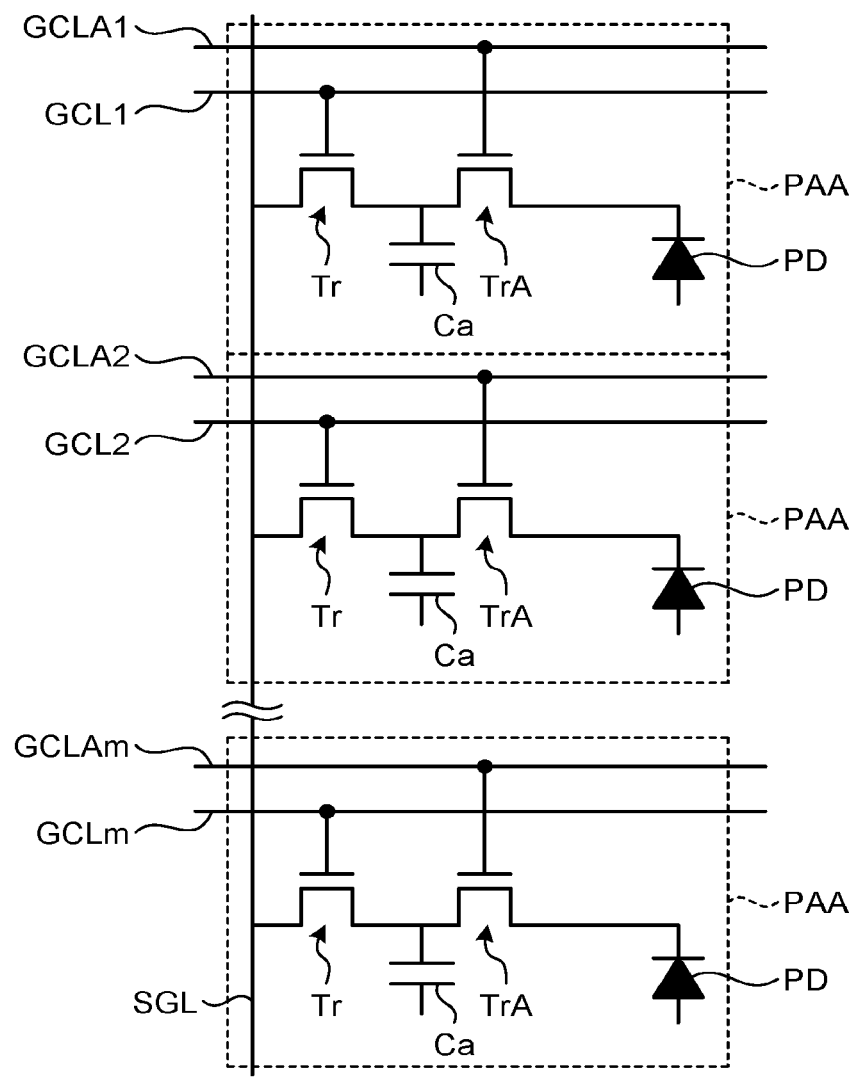
FIG. 17 is a circuit diagram illustrating partial detection areas according to a third embodiment.
Figure 18:
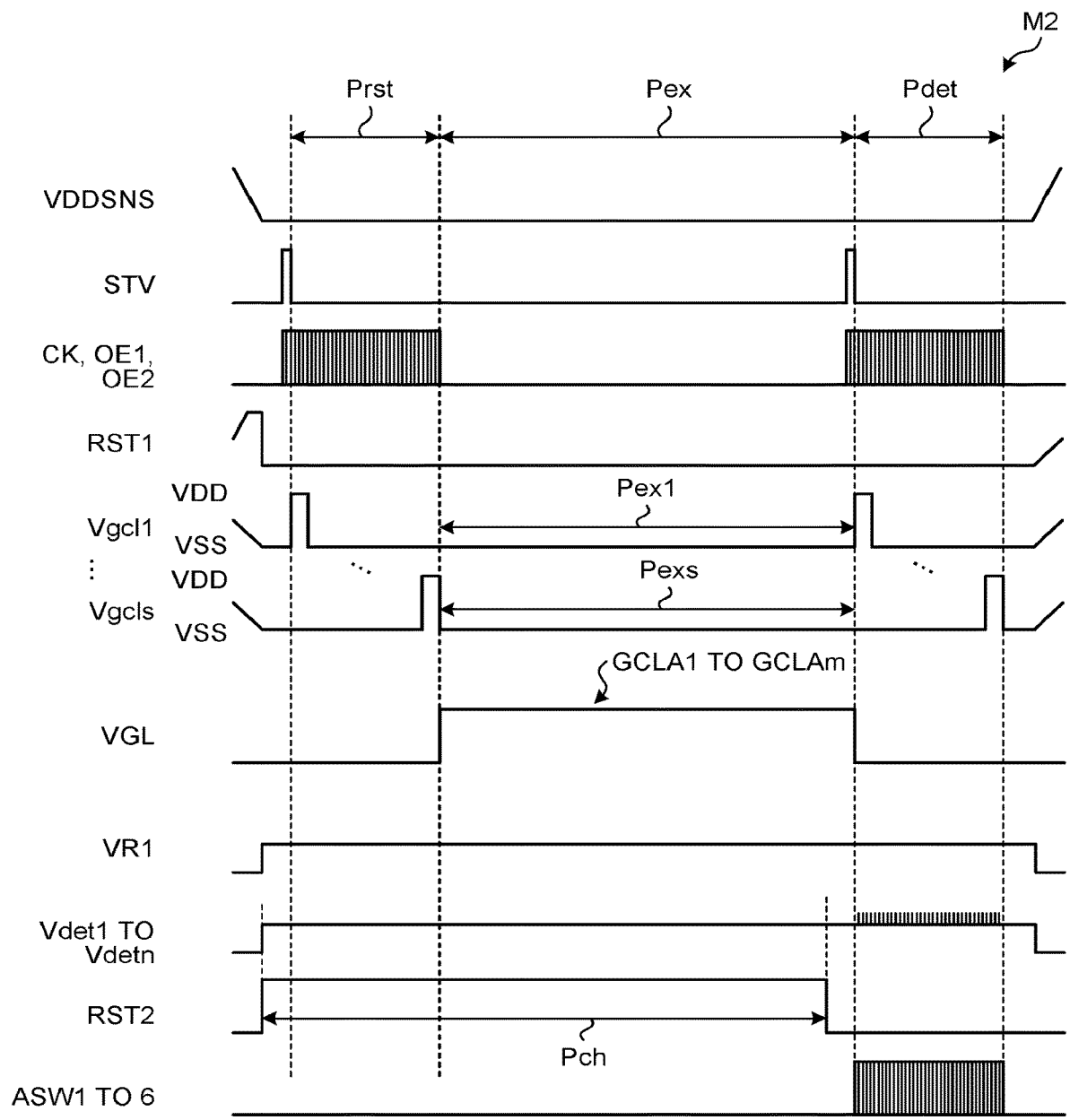
FIG. 18 is a timing waveform diagram illustrating an operation example of the fingerprint detection device according to the third embodiment.

FIG. 17 is a circuit diagram illustrating partial detection areas according to a third embodiment. FIG. 18 is a timing waveform diagram illustrating an operation example of the fingerprint detection device according to the third embodiment.

As illustrated in FIG. 17, each of the partial detection areas PAA includes a second switching element TrA and a corresponding one of second gate lines GCLA1, GCLA2, . . . , GCLAm. In the following description, the second gate lines GCLA1, GCLA2, . . . , GCLAm will each be simply referred to as a second gate line GCLA when need not be distinguished from one another.

A plurality of the second switching elements TrA are each provided for a corresponding one of the photodiodes PD. The second gate line GCLA is coupled to each of the second switching elements TrA. Specifically, the second gate line GCLA is coupled to the gate of the second switching elements TrA. The cathode of the photodiode PD is coupled to one of the source and the drain of the second switching element TrA. The capacitive element Ca and the source or the drain of the first switching element Tr are coupled to the other of the source and the drain of the second switching element TrA.

FIG. 18 illustrates the operation example of the fingerprint detection device 1 in the second detection mode M2. As illustrated in FIG. 18, during the reset period Prst, the gate line drive circuit 15 sequentially supplies the gate drive signals Vgcl to the fourth number (for example, six) of the first gate lines GCL. During the reset period Prst, the gate line drive circuit 15 also supplies a gate drive signal VGL at a low-level voltage to all the second gate lines GCLA.

As a result, during the reset period Prst, the first switching elements Tr coupled to the fourth number of the first gate lines GCL are sequentially turned on, and the capacitance of the capacitive elements Ca of all the partial detection areas PAA are reset. However, during the reset period Prst, all the second switching elements TrA are turned off, and the capacitive elements Ca are uncoupled from the photodiodes PD. That is, although the first switching elements Tr are turned on, no current flows from the photodiodes PD to the capacitive elements Ca, so that the exposure period Pex does not start.

During the exposure period Pex, the gate line drive circuit 15 simultaneously supplies the gate drive signal VGL at a high-level voltage to all the second gate lines GCLA. As a result, all the second switching elements TrA are turned on, and the capacitive elements Ca are coupled to the photodiodes PD. In the present embodiment, exposure periods Pex1, . . . , Pexs in the partial detection areas PAA are periods in which the gate drive signal VGL is at the high-level voltage, and the start timing and end timing of the exposure periods Pex1, . . . , Pexs are equal to one another. That is, the exposure periods Pex1, . . . , Pexs start when the gate drive signal VGL has shifted from the low-level voltage to the high-level voltage, and end when the gate drive signal VGL has shifted from the high-level voltage to the low-level voltage.

During the reading period Pdet, the fingerprint detection device 1 outputs the detection signals Vdet for each of the detection area groups PAG to the detection circuit 48 in the same manner as in the example described above.

In the present embodiment, since the exposure periods Pex1, . . . , Pexs are equal, distortion of the blood vessel image can be reduced when the change in the blood vessel image with time is detected in the second detection mode M2.

Fourth Embodiment

Figure 19:
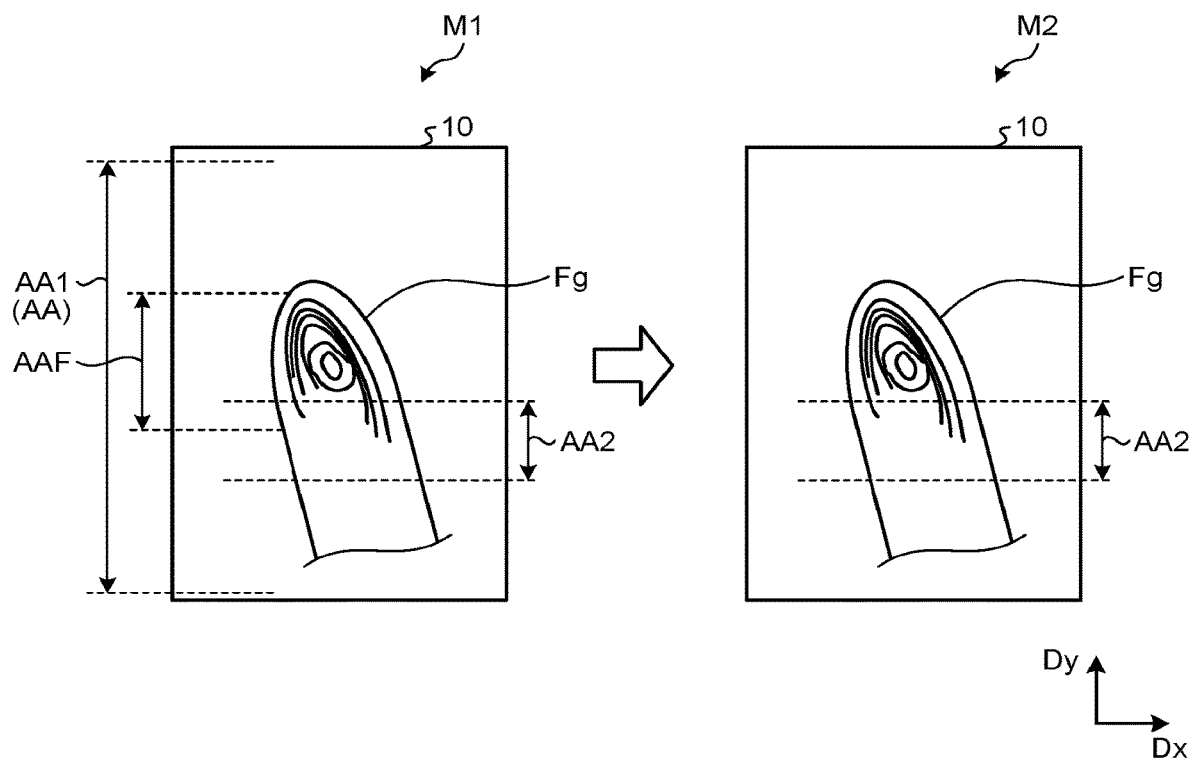
FIG. 19 is an explanatory diagram for explaining an operation example of the fingerprint detection device according to a fourth embodiment.
Figure 20:
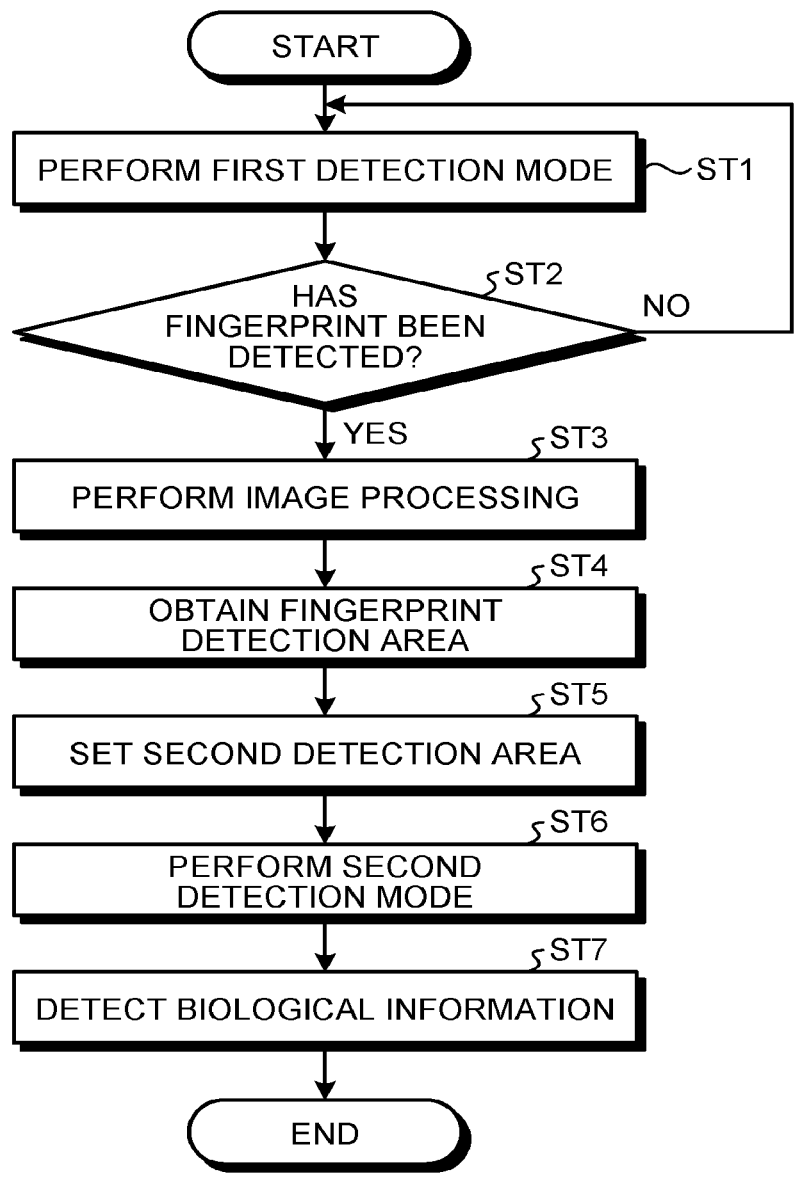
FIG. 20 is a flowchart for explaining the operation example of the fingerprint detection device according to the fourth embodiment.

FIG. 19 is an explanatory diagram for explaining an operation example of the fingerprint detection device according to a fourth embodiment. FIG. 20 is a flowchart for explaining the operation example of the fingerprint detection device according to the fourth embodiment.

As illustrated in FIGS. 19 and 20, the fingerprint detection device 1 performs the detection in the first detection mode M1 (Step ST1). The gate line drive circuit 15 sequentially supplies the gate drive signals Vgcl to the first gate lines GCL1 to GCLm, whereby the fingerprint detection device 1 performs the detection in a first detection area AA1. The first detection area AA1 is an area in which the detection in the first detection mode M1 is performed, and is an area overlapping the entire area of the detection area AA (refer to FIG. 2). The first detection area AA1 may, however, be a portion of the detection area AA.

The detector 40 (refer to FIG. 3) determines whether the fingerprint has been detected (Step ST2). If not (No at Step ST2), the fingerprint detection device 1 repeatedly performs the detection in the first detection mode M1.

If so (Yes at Step ST2), the image processor 49 performs image processing based on the detection signals Vdet (Step ST3) to generate the two-dimensional information representing the shape of the asperities on the surface of, for example, the finger Fg.

A detection area setter 11A (refer to FIG. 21) obtains a fingerprint detection area AAF based on the detection signals Vdet from the photodiodes PD in the first detection mode M1 (Step ST4). Specifically, the detection area setter 11A obtains the fingerprint detection area AAF based on positional information on the fingerprint of the finger Fg calculated by the detector 40. The fingerprint detection area AAF is an area in the second direction Dy in which the fingerprint of the finger Fg has been detected, as illustrated in FIG. 19.

Then, the detection area setter 11A sets a second detection area AA2 smaller than the first detection area AA1 (Step ST5). The detection area setter 11A sets, as the second detection area AA2, an area displaced in the second direction Dy from the fingerprint detection area AAF. The detection area setter 11A may calculate an amount of displacement between the second detection area AA2 and the fingerprint detection area AAF based on an offset value set in advance. The detection area setter 11A may set the second detection area AA2 based on the two-dimensional information (shape of the fingerprint) generated by the image processor 49 and information from the touchscreen panel 102.

The fingerprint detection device 1 performs the detection in the second detection mode M2 (Step ST6). At this time, the gate line drive circuit 15 supplies the gate drive signals Vgcl to the first gate lines GCL in the second detection area AA2. Through this operation, the fingerprint detection device 1 performs the detection in the second detection area AA2 smaller than the first detection area AA1.

The fingerprint detection device 1 can detect the biological information such as the blood vessel image and the pulsation based on the detection signals Vdet in the second detection mode M2 (Step ST7).

As described above, the fingerprint detection device 1 can perform the detection in the second detection mode M2 in the second detection area AA2 smaller than the first detection area AA1 based on the result of the detection in the first detection mode M1. As a result, the fingerprint detection device 1 can reduce time required for the detection in the second detection mode M2. Consequently, the fingerprint detection device 1 can repeatedly perform the detection in the second detection mode M2 in a short time, and therefore, can increase the S/N ratio, and can accurately detect the change in the biological information, such as the pulsation, with time.

Second Modification of Fourth Embodiment

Figure 21:
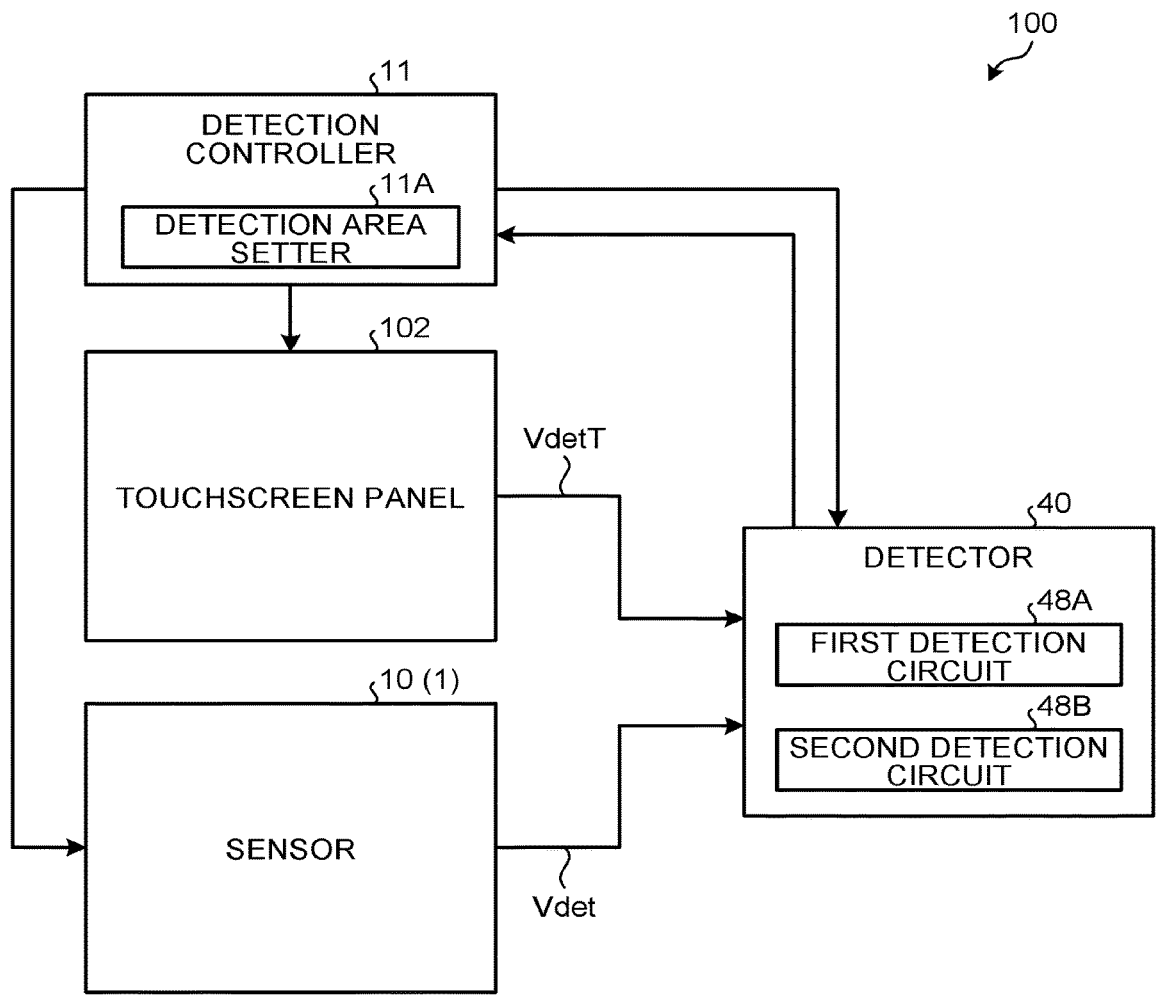
FIG. 21 is a block diagram illustrating a configuration example of the display device with a fingerprint detection device according to a second modification of the fourth embodiment.
Figure 22:
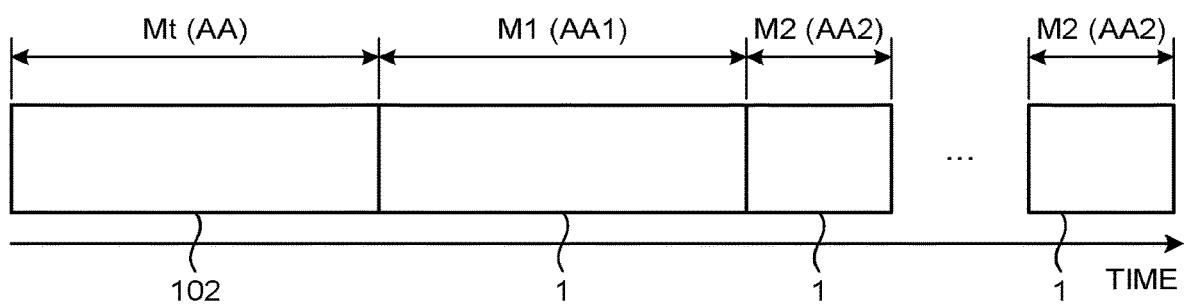
FIG. 22 is an explanatory diagram for explaining an operation example of the fingerprint detection device according to the second modification of the fourth embodiment.

FIG. 21 is a block diagram illustrating a configuration example of the display device with a fingerprint detection device according to a second modification of the fourth embodiment. FIG. 22 is an explanatory diagram for explaining an operation example of the fingerprint detection device according to the second modification of the fourth embodiment.

As illustrated in FIG. 21, the detector 40 in the display device 100 with a fingerprint detection device includes a first detection circuit 48A and a second detection circuit 48B. The first detection circuit 48A receives a detection signal VdetT from the touchscreen panel 102 and performs the same signal processing as that of the detection circuit 48 described above. The second detection circuit 48B is the same as the detection circuit 48 illustrated in FIG. 3 and will not be described in detail. Although not illustrated in FIG. 21, the detector 40 may include a signal processor and a coordinate extractor in each of the first detection circuit 48A and the second detection circuit 48B in the same manner as illustrated in FIG. 3.

The detection controller 11 includes the detection area setter 11A. The detection area setter 11A is an arithmetic circuit that sets the first detection area AA1 and the second detection area AA2. In the present embodiment, the detection controller 11 controls the detection operations of the touchscreen panel 102 and the fingerprint detection device 1. The detection controller 11 and the detector 40 may be made of one IC, or two or more ICs.

As illustrated in FIG. 22, the display device 100 with a fingerprint detection device causes the touchscreen panel 102 to perform a touch detection mode Mt to detect contact with or proximity to the detection area AA by, for example, the finger Fg. When the detector 40 has detected contact with or proximity to the detection area AA by, for example, the finger Fg in the touch detection mode Mt, the detector 40 calculates the positional information on the finger Fg based on the detection signal VdetT from the touchscreen panel 102. The detector 40 outputs the positional information on the finger Fg to the detection area setter 11A.

The detection area setter 11A sets the first detection area AA1 based on the positional information on the finger Fg. In other words, the detection area setter 11A sets the first detection area AA1 based on the detection signal VdetT from the touchscreen panel 102. The detection area setter 11A sets the first detection area AA1 including at least an area overlapping the finger Fg. The first detection area AA1 is an area smaller than the detection area AA. Then, the fingerprint detection device 1 performs the detection in the first detection mode M1 and the second detection mode M2 in the same manner as in the operation example illustrated in FIGS. 19 and 20.

In this modification, the first detection area AA1 in which the detection is performed in the first detection mode M1 can be limited to a smaller area than that of the above-described fourth embodiment based on the positional information on the finger Fg obtained by the touchscreen panel 102. As a result, time required for the detection in the first detection mode M1 can be reduced, and time required for the signal processing on the detection signals Vdet and the image processing can also be reduced.

Fifth Embodiment

Figure 23:
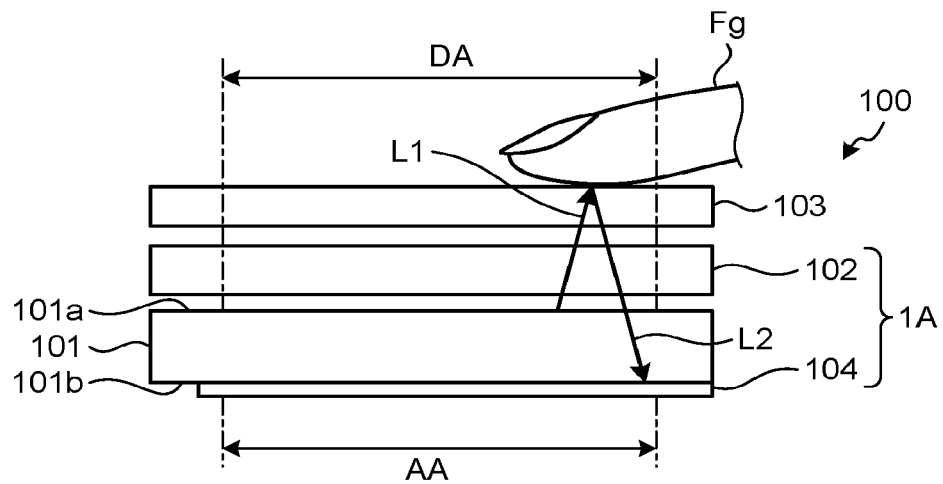
FIG. 23 is a sectional view illustrating a schematic sectional configuration of a display device with a fingerprint detection device according to a fifth embodiment.
Figure 24:
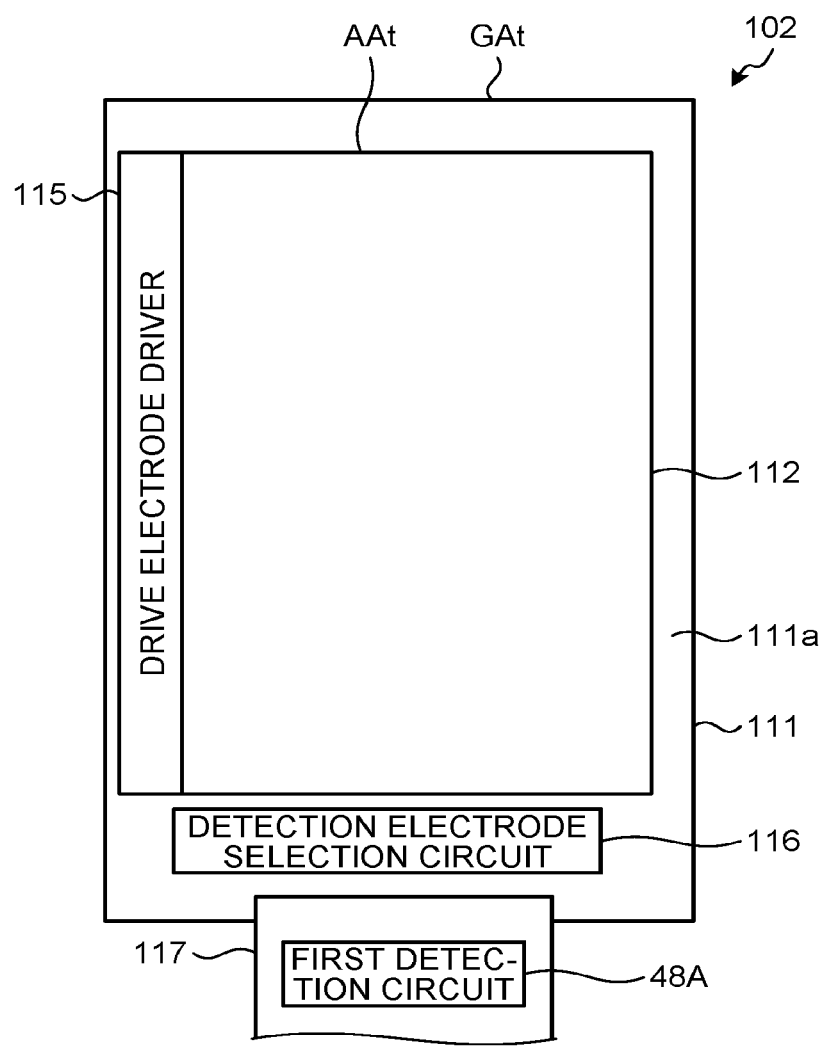
FIG. 24 is a plan view illustrating a touchscreen panel included in the display device with a fingerprint detection device according to the fifth embodiment.
Figure 25:
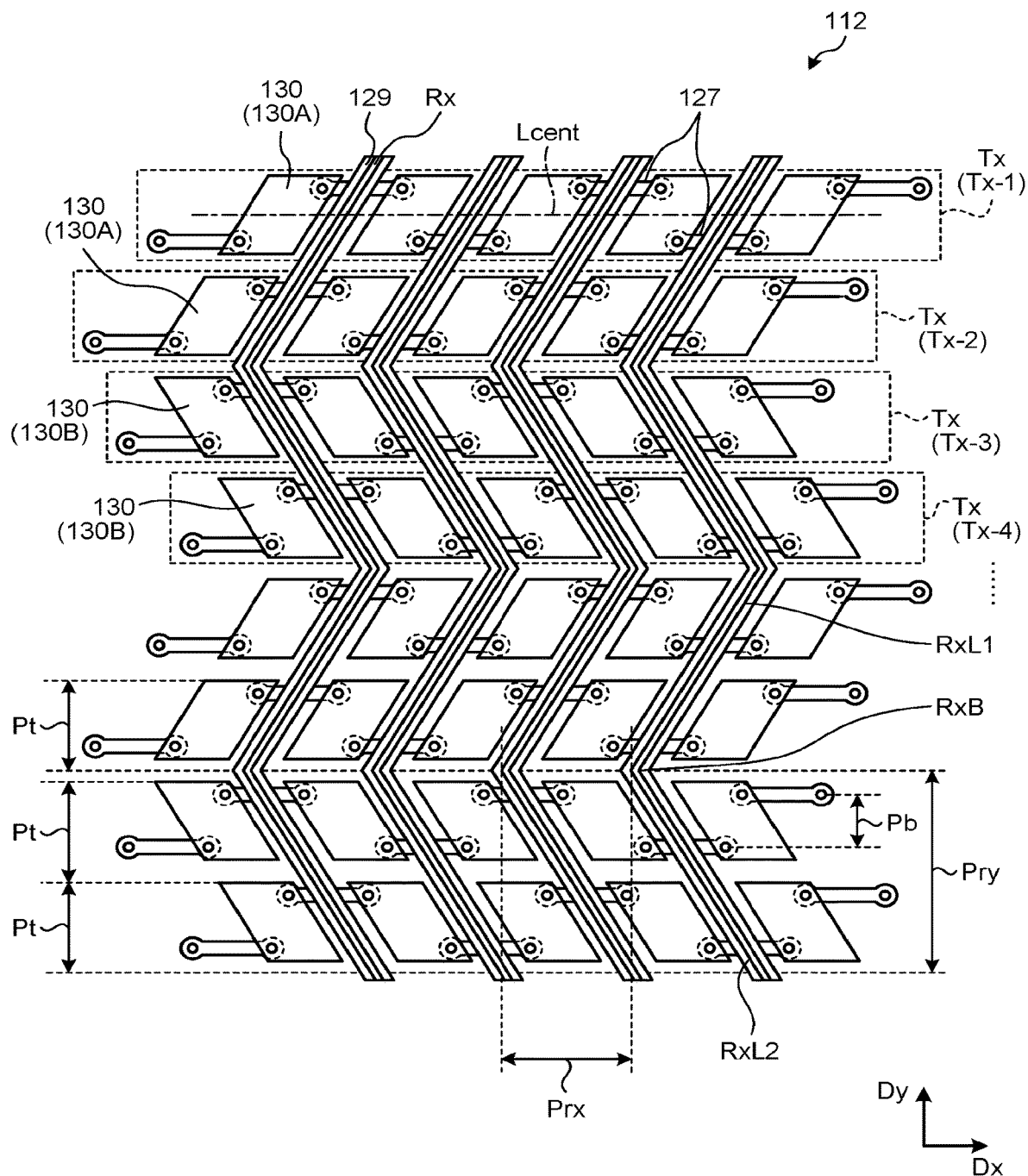
FIG. 25 is a plan view illustrating drive electrodes and detection electrodes of the touchscreen panel.

FIG. 23 is a sectional view illustrating a schematic sectional configuration of a display device with a fingerprint detection device according to a fifth embodiment. FIG. 24 is a plan view illustrating the touchscreen panel included in the display device with a fingerprint detection device according to the fifth embodiment. FIG. 25 is a plan view illustrating drive electrodes and detection electrodes of the touchscreen panel.

In the present embodiment, a fingerprint detection device 1A includes the touchscreen panel 102 and an optical sensor 104. The touchscreen panel 102 performs the touch detection to detect the contact or proximity of the finger Fg and the fingerprint detection to detect the asperities on the surface of the finger Fg based on the control signals from the detection controller 11 (first detection mode M1). The optical sensor 104 has the same configuration as that of the above-described fingerprint detection device 1 and will not be described in detail. However, the optical sensor 104 performs the detection in the second detection mode M2 and does not perform the detection in the first detection mode M1.

As illustrated in FIG. 24, the touchscreen panel 102 includes a second substrate 111, a sensor 112 provided on a one surface 11a side of the second substrate 111, a drive electrode driver 115, a detection electrode selection circuit 116, and the first detection circuit 48A. The sensor 112 includes drive electrodes Tx (refer to FIG. 25) and detection electrodes Rx (refer to FIG. 25).

The second substrate 111 is a light-transmitting glass substrate that can transmit visible light. Alternatively, the second substrate 111 may be a light-transmitting resin substrate or a resin film formed of a resin such as polyimide. The sensor 112 is a light-transmitting sensor.

The drive electrode driver 115 is a circuit that supplies a drive signal to each of the drive electrodes Tx of the sensor 112 based on a control signal supplied from the detection controller 11. The drive signal supplied to the drive electrode Tx is, for example, an alternating current rectangular wave. The detection electrode selection circuit 116 selects any one of the detection electrodes Rx of the sensor 112 based on a control signal supplied from the detection controller 11 and couples the detection electrode Rx to the first detection circuit 48A. The first detection circuit 48A is provided on a flexible printed circuit board 117. However, the first detection circuit 48A may be provides on the flexible printed circuit board 71 or the control board 121 coupled to the optical sensor 104.

The following describes shapes of the detection electrode Rx and the drive electrode Tx. As illustrated in FIG. 25, the detection electrode Rx intersects the drive electrodes Tx. Electrostatic capacitances are formed between the detection electrodes Rx and the drive electrodes Tx. The touchscreen panel 102 can perform the touch detection and the fingerprint detection using what is called a mutual-capacitance method (mutual method).

The detection electrode Rx has a zigzag line shape as viewed from a direction orthogonal to the second substrate 111. The detection electrode Rx extends in the second direction Dy in a zigzagging manner. The detection electrode Rx is formed of a metal material. For example, aluminum, molybdenum, or an alloy of these materials is used as a material of the detection electrode Rx. The detection electrode Rx has a plurality of first linear portions RxL1, a plurality of second linear portions RxL2, and a plurality of bent portions RxB. The second linear portions RxL2 extend in a direction intersecting the first linear portions RxL1. The bent portions RxB couple the first linear portions RxL1 to the second linear portions RxL2.

In one example, the first linear portions RxL1 extend in a direction intersecting the first direction Dx and the second direction Dy. The second linear portions RxL2 also extend in a direction intersecting the first direction Dx and the second direction Dy. The first linear portions RxL1 and the second linear portions RxL2 are arranged so as to be symmetrical with respect to a virtual line (not illustrated) parallel to the first direction Dx.

Pry denotes an arrangement interval of the bent portions RxB of each of the detection electrodes Rx in the second direction Dy. Prx denotes an arrangement interval of the bent portions RxB between the adjacent detection electrodes Rx in the first direction Dx. In the present embodiment, for example, a relation Prx<Pry holds.

As illustrated in FIG. 25, each of the drive electrodes Tx (for example, Tx-1, Tx-2, Tx-3, Tx-4, . . . ) arranged in the second direction Dy includes a plurality of electrode portions 130 and a plurality of coupling portions 127. In each of the drive electrodes Tx, the electrode portions 130 are arranged in the first direction Dx, and are arranged so as to be spaced from one another. In each of the drive electrodes Tx, each of the coupling portions 127 couples electrode portions among the electrode portions 130 adjacent in the first direction Dx to each other. When viewed from a direction of the normal to the second substrate 111 (refer to FIG. 24), each of the detection electrodes Rx passes through an interval between the adjacent electrode portions 130 and intersects the coupling portion 127. The drive electrodes Tx are formed of a light-transmitting conductive material such as ITO.

Pb denotes an arrangement interval of the coupling portions 127 in the second direction Dy. The arrangement interval Pb of the coupling portions 127 is preferably 0.5 times an arrangement interval Pt of the drive electrodes Tx. In each of the drive electrodes Tx, the coupling portions 127 are preferably alternately arranged on one side and on the other side with respect to a center line Lcent parallel to the first direction Dx and passing through the centers of the electrode portions 130. With this configuration, the coupling portions 127 having lower light transmittance than that of the electrode portions 130 are not linearly arranged, so that the sensor 112 can reduce generation of an unintended pattern such as a moire pattern.

FIG. 25 is merely an example, and the touchscreen panel 102 may have another configuration. For example, the touchscreen panel 102 may perform the touch detection and the fingerprint detection using a self-capacitance method (self method). In this case, the touchscreen panel 102 can perform the detection based on a change in capacitance of each of the detection electrodes arranged in a matrix having a row-column configuration.

As described above, the fingerprint detection device 1A of the present embodiment includes the optical sensor 104 and the touchscreen panel 102. The optical sensor 104 includes the first substrate 21 and the photoelectric conversion elements (photodiodes PD) that are provided to the first substrate 21 and each output the signal corresponding to the light emitted thereto. The touchscreen panel 102 is a capacitive touchscreen panel including the second substrate 111 facing the first substrate 21 and the detection electrodes Rx provided to the second substrate 111. The touchscreen panel 102 performs the touch detection mode Mt of detecting the contact or proximity of the detection target object and the first detection mode M1 of detecting the asperities on the surface of the detection target object at a detection pitch smaller than a detection pitch in the touch detection mode Mt. The optical sensor 104 performs the second detection mode M2 of detecting the information in the detection target object at a detection pitch larger than the detection pitch in the first detection mode M1.

While the preferred embodiments of the present disclosure have been described above, the present disclosure is not limited to the embodiments described above. The content disclosed in the embodiments is merely an example, and can be variously modified within the scope not departing from the gist of the present disclosure. Any modifications appropriately made within the scope not departing from the gist of the present disclosure naturally belong to the technical scope of the present disclosure.

What is claimed is:

1. A fingerprint detection device comprising:
   a substrate;
   a plurality of photoelectric conversion elements provided to the substrate, each being configured to output a signal corresponding to light emitted thereto;
   a plurality of signal lines coupled to the photoelectric conversion elements;
   a detection circuit electrically coupled to the photoelectric conversion elements through the signal lines; and
   a signal line selection circuit configured to switch a number of the signal lines to be coupled to the detection circuit,
   wherein the signal line selection circuit is configured to
   sequentially couple the signal lines to the detection circuit in units of a first number of the signal lines SGL in a first detection mode, and
   simultaneously couple a second number of the signal lines to the detection circuit in a second detection mode of detecting the light at a detection pitch different from that in the first detection mode, the second number being larger than the first number;
   further comprising:
   a plurality of first switching elements provided for the photoelectric conversion elements, respectively;
   a plurality of first gate lines coupled to the first switching elements; and
   a gate line drive circuit configured to supply drive signals to the first gate lines,
   wherein the gate line drive circuit is configured to
   supply the drive signals to a third number of the first gate lines in the first detection mode, and
   simultaneously supply the drive signals to a fourth number of the first gate lines in the second detection mode, the fourth number being different from the third number;
   further comprising:
   a plurality of second switching elements provided for the photoelectric conversion elements, respectively; and a plurality of second gate lines coupled to the second switching elements, wherein the gate line drive circuit is configured to simultaneously supply the drive signals to all the second gate lines.

2. The fingerprint detection device according to claim 1, wherein one of a source and a drain of each of the second switching elements is coupled to a corresponding one of the photoelectric conversion elements, and wherein the other one of the source and the drain of the second switching element is coupled to a capacitive element and a source or a drain of a corresponding one of the first switching elements.

3. A fingerprint detection device comprising:

a substrate;

a plurality of photoelectric conversion elements provided to the substrate, each being configured to output a signal corresponding to light emitted thereto;

a plurality of signal lines coupled to the photoelectric conversion elements;

a detection circuit electrically coupled to the photoelectric conversion elements through the signal lines; and a signal line selection circuit configured to switch a number of the signal lines to be coupled to the detection circuit, wherein the signal line selection circuit is configured to
 sequentially couple the signal lines to the detection circuit in units of a first number of the signal lines SGL in a first detection mode, and
 simultaneously couple a second number of the signal lines to the detection circuit in a second detection mode of detecting the light at a detection pitch different from that in the first detection mode, the second number being larger than the first number;

further comprising:

a plurality of first switching elements provided for the photoelectric conversion elements, respectively;

a plurality of first gate lines coupled to the first switching elements; and a gate line drive circuit configured to supply drive signals to the first gate lines, wherein the gate line drive circuit is configured to
 supply the drive signals to a third number of the first gate lines in the first detection mode, and
 simultaneously supply the drive signals to a fourth number of the first gate lines in the second detection mode, the fourth number being different from the third number;

further comprising:

a detection area setter configured to set a first detection area in which detection in the first detection mode is to be performed and a second detection area in which detection in the second detection mode is to be performed, wherein the detection area setter is configured to set the second detection area smaller than the first detection area based on the signals from the photoelectric conversion elements in the first detection mode, and wherein the gate line drive circuit is configured to supply the drive signals to the first gate lines in the second detection area.

4. The fingerprint detection device according to claim 3, further comprising a touchscreen panel configured to detect contact or proximity of a detection target object, wherein the detection area setter is configured to set the first detection area based on a detection signal from the touchscreen panel.

5. A fingerprint detection device comprising:

a substrate;

a plurality of photoelectric conversion elements provided to the substrate, each being configured to output a signal corresponding to light emitted thereto;

a plurality of signal lines coupled to the photoelectric conversion elements;

a detection circuit electrically coupled to the photoelectric conversion elements through the signal lines; and a signal line selection circuit configured to switch a number of the signal lines to be coupled to the detection circuit, wherein the substrate comprises a detection area provided with the photoelectric conversion elements and a peripheral area between an outer circumference of the detection area and edges of the substrate, wherein the peripheral area is provided with a light source configured to emit light, and wherein the photoelectric conversion elements are configured to
 detect visible light reflected by a detection target object in a first detection mode, and
 detect light that is emitted from the light source and reflected by the detection target object in a second detection mode.

\* \* \* \* \*